US007332341B2

(12) United States Patent
Royer et al.

(10) Patent No.: US 7,332,341 B2
(45) Date of Patent: Feb. 19, 2008

(54) METHODS FOR PRODUCING HETEROLOGOUS POLYPEPTIDES IN TRICHOTHECENE-DEFICIENT FILAMENTOUS FUNGAL MUTANT CELLS

(75) Inventors: John C. Royer, Lexington, MA (US); Lynne M. Christanson, Aptos, CA (US); Gregory A. Gambetta, Davis, CA (US); Howard Brody, Davis, CA (US); Suzanne M. Otani, Elk Grove, CA (US); Wendy T. Yoder, Davis, CA (US)

(73) Assignee: Novozymes, Inc., Davis, CA (US)

( * ) Notice: Subject to any disclaimer, the term of this patent is extended or adjusted under 35 U.S.C. 154(b) by 0 days.

(21) Appl. No.: 11/095,491

(22) Filed: Mar. 31, 2005

(65) Prior Publication Data

US 2005/0181480 A1 Aug. 18, 2005

Related U.S. Application Data

(60) Division of application No. 09/316,080, filed on May 20, 1999, now Pat. No. 6,180,366, which is a continuation-in-part of application No. 09/082,217, filed on May 20, 1998, now abandoned.

(51) Int. Cl.
*C12N 15/74* (2006.01)
*C12N 1/00* (2006.01)
*C07H 21/04* (2006.01)

(52) U.S. Cl. ...................... 435/471; 435/476; 435/477; 435/484; 435/254.7; 536/23.74

(58) Field of Classification Search ..................... None
See application file for complete search history.

(56) References Cited

U.S. PATENT DOCUMENTS 5,302,527 A * 4/1994 Birkett et al. ............ 435/254.5
5,594,119 A * 1/1997 Yaver et al. ............... 536/23.2
6,337,201 B1 * 1/2002 Yanai et al. ................ 435/200
6,383,781 B1 * 5/2002 Christensen et al. ....... 435/69.1

OTHER PUBLICATIONS

Scheid, O.M., Either/or selection markers for plant trasnformation, Nature Biotechnology, 2004, vol. 22(4), pp. 398-399.*

Vicentz et al, Constitutive expression of nitrate reductase allows normal growth and development of *Nicotiana plumbaginifolia* plants, EMBO J, 1991, vol. 10, pp. 1027-1035.*

Horng et al, Development of a homologous transformation system for *Aspergillus parasiticus* with the gene encoding nitrate reductase, Mol Gen Genet, 1990, vol. 224, pp. 294-296.*

Brown et al, Project Reprot: FY 1993, Jan. 1994, pp. 1-32.*

Pereira et al, Characterization , regulation and phylogenetic analysis of the *Penicillium griseroroseum* nitrate reductase gene and its use as selection marker for homologous transformation, Can J Microbiol, 2004, vol. 50, pp. 891-900.*

Perdomo et al, Tobacco Nia2 cDNA functionally complements a *Hansenula polymorpha* yeast mutant lacking nitrate reductase. A new expression system for the study of plant proteins involved in nitrate assimilation, Plant Molecular Biology, 2002, vol. 50, pages.*

Desjardins et al, Effect of Gene Disruption of Trichodiene Synthase on the Virulence of *Gibereralla pulcaris*, Molecular Plant-Microbe Interactions, vol. 5(3), 1992, pp. 214-222.*

O'Donnell et al, Molecular Phylogenetic, Morphological, and Mycotoxin Data Support Reidentification of the Quorn Mycoprotein Fungus as *Fusarium venenatum*, Fungal Genetics and Biology, 1998, vol. 23, pp. 57-67.*

Mule et al, Clustering of Tricothecene-Producing Fusarium Strains Determined form 28S Ribosomal DNA sequences, Applied and Environmental Microbiology, 1997, vol. 63(5), pp. 1842-1846.*

Daboussi et al, Transformation of seven species of filamentous fungi using the nitrate reductase gene of *Aspergillus nidulans*, Current Geneti, 1989, vol. 15, pp. 453-456.*

Desjardins, Hohn, and McCormick, 1993, Microbiological Reviews 57: 595-604.

Hohn and Beremand, 1989, Gene 79: 131-138.

Hohn and Desjardins, 1992, Molecular Plant-Microbe Interactions 5: 249-256.

Proctor et al., 1995, Molecular Plant-Microbe Interactions 4: 593-601.

Trapp et al., 1995, Journal of Cellular Biochemistry Supplement 19B: 154.

Fekete et al., 1997, Mycopathologia 138: 91-97.

McCormick et al., 1996, Applied and Environmental Microbiology 62: 353-359.

Hohn et al., 1995, Molecular and General Genetics 248: 95-102.

Proctor et al., 1995, Applied and Environmental Microbiology 61: 1923-1930.

Alexander et al., 1997, Applied and Environmental Microbiology 64: 221-225.

Kimura et al., 1998, Journal of Biological Chemistry 273: 1654-1661.

* cited by examiner

*Primary Examiner*—Joe Woitach
*Assistant Examiner*—Maria Marvich
(74) *Attorney, Agent, or Firm*—Robert L. Starnes

(57) ABSTRACT

The present invention relates to mutants cells comprising a marker-free modification of a gene, and methods for obtaining and using such mutant cells.

8 Claims, 16 Drawing Sheets

```
GAATTCTCTCAGTCGGCCTCATCTGGCAGGTGCTAATATATTCTA 45
CCCGCGCTTGGCTACCTATGCCACACACAAAGCTTCATGTTTGGT 90
TCATATCGTATACTCGCTTCAACAGTTCTGCGGGTACGACTCTCG 135
TATGGATGTAATAAACAAATGTTCCGACCTATTATGCCGAGTTAC 180
CGTGGACAATTATCGGGCCGGAAAAGAATGCATTTGTGAATTGTA 225
ATCCTGCCTGTTTGTGGAGTGATAAGTGACATATTGGAAAAGTCG 270
TCAAGCAATTGGAGGTTTCATCAACTGTGGAGTCATCGTTTTGGG 315
CAAACAATACTATGTAGGGTAGGCTTCTGCTGCAGCATCAATGAC 360
TCGTTTGGATCGAGTCCTTTTGTTGCCAAGGCGTATGGGGCCTGC 405
AGGGAACGAGTCAGTCGTATCAGGCCGGTGAGGCAAATGCCGTTT 450
CGCAGCAGCTATCATTTGTCGCGGGATTTTCGCGAAGCTTTGCGT 495
GACGAGTCAAATCCGCACATCTTGATTCATGAGTTGTTGAATTTA 540
GCTGTTCATTCGTGAGTGGCTAAAGCGTATCTAGTCGATTGTCAA 585
ATTCAGACTTGACAGGTCCCTTGATGAATGAGACGTCGGATGTCC 630
CTAGCCGAGATGCGGATTGTGACAACGGAAGAGACAGGGGCAGGG 675
TTCATGGGTGTTGAACCTTGTTCACTGAAACGGTGATGTCTTTGG 720
TCTACAAAGTATCCTTCACATGTCTCTGTTCCCAGACCACGTGGT 765
TATTCTGGCATCCGGGTCCTATTGATTGGCTGATTTCTTGCACTG 810
ATACATACAAATAAGTCCAAGACTGTATTCTACTGGCAAAATTAT 855
GCCGACAAGGGGAAATCATTCTGAATTAGTGATGAAGCATGCCGT 900
CGAAGCCGAAGAGAAACTTTGCGCAGCAACTGGAAAGACCTGTGG 945
GCTGTAGAGCGCACAGCACGGTAGTAAGACCTACGGCCCTGGTAT 990
CATGGTTGTAGCCTCTTCCGTATTGCTCACATATCCACCGGTTTT 1035
CTACATAAACAGTCTGAGTCCTGATAGTGGATATTATATCTTCCA 1080
GGACCTAGTCTAGGTAGTAGTCGGCATTTGAAACGCCTAGTGGCA 1125
AGAGATCGCTTAGCCTCCAGCCTGGCAATATCGCGGCTTCCTCAG 1170
GTTGTACCACGAATGATGATCTCAATTGTGCTTCCCCTGTCGTGA 1215
ATTTGCTAGTGCGACGGGACTTGCCAGGCTTACGGCACCTACAAG 1260
TCGCGCCAGCCTTCTGACAGTGATTGTATGCAAGATCGTCATTAG 1305
TTATGATTAAGCTTTGATAAACAAGAGCGCCACAGCCTTTCTTTA 1350
ACTCCGACAACCTCAACGGTGACATGCATACCGCGTGACACTATT 1395
TCCCATGGTGTGAACACCATCAATGACTTAGAGTAGATAACCACT 1440
TGAAACTTCTAGAAATGTCCAAGAAACTACACTCAGTGTTTCATA 1485
GAACTAAGACAATGTTCATTGAAGGATGGGATTTGAGACTCCGTA 1530
CTGCTTCACCTCGGAAAATAAGCACTGTTTAGCACCCGTTAAGCC 1575
AAGTCCTTCAAACGTGGGGACGGATTTAACCAACAGCAGAGTGGA 1620
TAAGCCTGTACTCTACTCATTGAATGTATATAATACATTGCTAGG 1665
TACATACGCAGCTTTCAGGCACAGATAACGAAGATCTTAGGGTAG 1710
ATTCCAAAACATCGGAAGGGGTCACAGATCGCACTAGCTACTATG 1755
CCATCCAGAGCCTCTTGCTAACCAAACAGAGCTAAGTCGCTTAAC 1800
```

Fig. 2A

```
CCTTATTCAAAGAACACAGTTGTATTGTGCATCCGGGATCTAACT 1845
GTCTTGGACAAGCGTGTTCTGTATCCGTAACGGCTGGTGGTTTTG 1890
TAGGGTATGATAGAATGGTTGCACTTAAGGCCTGTCGACTAGGTA 1935
AGCTTTTCCCAGGGAAGAATAAAACACCGCGGCTGCTTAGACAAG 1980
TGAGGCTTTCTTCTCCGTCAACAAACTGCCGTCTCACTAGTCCAA 2025
ACTTGGTCACGGACAACAGCCGAACTCAAACATTTAGCCTCAGGA 2070
TTCATCCCTAGCTTTAGGCCTACTCCTCGTCCCTTGACACCGGGA 2115
TGTAGTTCCTATCGCTTGCGTAGCTCTTTACTGCATGTGCCGAGC 2160
TAAAGATAAAATCGGACTAAAGATTCGTTCCGGGAGCCGAATGCT 2205
TTCTCAAGCTCGTCGTGTTGCAGGGGATGGAAGACCTCCAGCGTA 2250
CGTCACGGTCTCTATCACTACGAATTTGCTGGGAAGGCTATTTGC 2295
ATTAATGTCAAGTCAATTATTAGGCCTAACAACACAAGTTTAACT 2340
AAAGATTGTGGATGGTTGACATTTGCCATATGTTGATATATAGTT 2385
GATAGCAACAGCACTTTGCAATAGGACAATAATAGCGACTTGACT 2430
TGAAAATTCGCAAAGAACTGTTATAAATCATTATACCATTATCAT 2475
CATGGAGAACTTTCCCACTGAGTATTTTCTCAACACTTCTGTGCG 2520
   M  E  N  F  P  T  E  Y  F  L  N  T  S  V  R
CCTTCTCGAGTACATTCGATACCGAGATAGCAATTATACCCGGGA 2565
   L  L  E  Y  I  R  Y  R  D  S  N  Y  T  R  E
AGAGCGTATCGAGAATTTGCACTATGCTTACAACAAGGCTGCTCA 2610
   E  R  I  E  N  L  H  Y  A  Y  N  K  A  A  H
TCACTTTGCTCAGCCACGACAACAGCAGCTGCTCAAGGTAGACCC 2655
   H  F  A  Q  P  R  Q  Q  Q  L  L  K  V  D  P
TAAGCGACTACAGGCTTCCCTCCAAACTATTGTTGGCATGGTGGT 2700
   K  R  L  Q  A  S  L  Q  T  I  V  G  M  V  V
ATACAGTTGGGCAAAGGTCTCCAAAGAGTGTATGGCGGATCTATC 2745
   Y  S  W  A  K  V  S  K  E  C  M  A  D  L  S
TATTCATTACACGTACACACTCGTTTTGGATGACAGCAGCGATGA 2790
   I  H  Y  T  Y  T  L  V  L  D  D  S  S  D  D
TCCGTATCCAGCCATGATGAACTATTTCAACGATCTTCAGGCTGG 2835
   P  Y  P  A  M  M  N  Y  F  N  D  L  Q  A  G
ACGAGAACAGGCCCACCCATGGTGGGCGCTTGTTAATGAGCACTT 2880
   R  E  Q  A  H  P  W  W  A  L  V  N  E  H  F
TCCCAATGTCCTTCGACATTTTGGTCCCTTCTGCTCATTGAACCT 2925
   P  N  V  L  R  H  F  G  P  F  C  S  L  N  L
TATCCGCAGCACTCTTGACTGTAAGTACCCTGGCTCTATTATTTC 2970
   I  R  S  T  L  D
ACCGCCTTAATAAGCTAACAGTGATGGAATTATAGTTTTTGAGGG 3015
                                      F  F  E  G
```

Fig. 2B

```
ATGCTGGATCGAGCAGTACAACTTTGGAGGATTTCCAGGATCTCA 3060
 C  W  I  E  Q  Y  N  F  G  G  F  P  G  S  H
TGACTATCCTCAGTTTCTTCGACGCATGAATGGCTTGGGTCACTG 3105
 D  Y  P  Q  F  L  R  R  M  N  G  L  G  H  C
TGTCGGGGCTTCTTTGTGGCCCAAAGAGCAGTTTGATGAGAGAGG 3150
 V  G  A  S  L  W  P  K  E  Q  F  D  E  R  G
TCTATTCCTTGAAATCACATCAGCCATTGCTCAGATGGAGAACTG 3195
 L  F  L  E  I  T  S  A  I  A  Q  M  E  N  W
GATGGTCTGGGTCAATGATCTCATGTCTTTCTACAAGGAGTTCGA 3240
 M  V  W  V  N  D  L  M  S  F  Y  K  E  F  D
TGATGAGCGTGACCAGATCAGTCTCGTCAAGAACTACGTCGTCTC 3285
 D  E  R  D  Q  I  S  L  V  K  N  Y  V  V  S
TGATGAGATCACTCTCCACGAAGCTTTAGAGAAGCTCACCCAGGA 3330
 D  E  I  T  L  H  E  A  L  E  K  L  T  Q  D
CACTCTACACTCGTCCAAGCAGATGGTAGCTGTCTTCTCTGACAA 3375
 T  L  H  S  S  K  Q  M  V  A  V  F  S  D  K
GGACCCTCAGGTGATGGACACGATTGAGTGCTTCATGCACGGCTA 3420
 D  P  Q  V  M  D  T  I  E  C  F  M  H  G  Y
TGTCACGTGGCACTTGTGCGATCACAGGTACCGTCTGAATGAGAT 3465
 V  T  W  H  L  C  D  H  R  Y  R  L  N  E  I
CTACGAAAAGGTCAAAGGACAAAAGACCGAGGACGCTCAGAAGTT 3510
 Y  E  K  V  K  G  Q  K  T  E  D  A  Q  K  F
CTGCAAGTTCTATGAGCAGGCTGCTAACGTCGGAGCCGTTTCGCC 3555
 C  K  F  Y  E  Q  A  A  N  V  G  A  V  S  P
CTCGGAGTGGGCTTATCCACCTATTGCGCAACTGGCAAACATTCG 3600
 S  E  W  A  Y  P  P  I  A  Q  L  A  N  I  R
GTCCAAGGATGTGAAGGATGTGAAGGATGTGAAGGAGATTCAGAA 3645
 S  K  D  V  K  D  V  K  D  V  K  E  I  Q  K
GCCTCTGCTGAGCTCAATTGAGCTAGTGGAATGACCGACGGTGAG 3690
 P  L  L  S  S  I  E  L  V  E
ATGGAAGTATGTTTTGCGGGTACTCGCTAGGAGAATACTGGTCGT 3735
TTATCATGATTACAAATAGCTTGGTTATGTTTTTATTAGCATTTA 3780
CAGTTGAACAAGGATAATTACTACTGAATAGGCAGCTGAAACTGA 3825
TGTCTGTAACTCCAGCCTGTTATTCCACTTGCCTGCAGGTCTTTG 3870
CATGGCCAAGTCATACATACCTGTTACGGTGTCGGTGCGACAGGG 3915
CTATCCATACCCCGGCCCAGCCTGCAGTAGAGCAGGCGTCACGGC 3960
CTGTAGTGCGCTGCGGGAATCTTCCACCCGTTCGGATGTGGGAAG 4005
TTTTGTTGTCCTCGGGGCTAACACATTCCAACCATTAATTGATCT 4050
TCAAAACGCTTGCATTTGCTCTATATGGCCGGCCTTGATCCTTGT 4095
ATATTTTCACCATCTGACATTTTCTGCACAAGGCGTACAGAAACC 4140
```

Fig. 2C

```
ACACGAGGTAAAGTTTCATGGCCGCTTGGCCACTATTGGAAACAC 4185
GACACACATGTTAAACTCTATCCTTGCATTATATTGTAACATCGC 4230
CTAACATCTCCACGCACTATTCCTTTGCGTTCCTTATTCATCCTC 4275
AACTGTATGCCAACCAACAATCATCAAATTATTATTGCAGTTAGT 4320
CATCATGGATTTCCCAAAGCCGAGGCAGGTTAGAGAGACGAGCCT 4365
GTTGATGTACTACCTGGACGTCGTGTTTTCTCTACAATGCATTAC 4410
CCCAAACAACAATTGTCTGGGCAAGAGAGAGTGGCTGTTGACTAT 4455
ACTAACCTCTGCTCGGCCTACGTACTATGCAACATTGTGCCTGGC 4500
CCTCCTTTATAAAGAATCCCTCTCAAGCCCTTGCAGAGCCGAACA 4545
AGCGGTAGTATGGAAGAGAGAAAAGACCTACTACTACATTCTTGC 4590
GCTCCAAGAGTCTCAGAAGCTGTTGGGTGGACTCGACAAGACTTT 4635
TGGTATCACAAGGCTGAAGGGGACCGTCGTTGCCCTTGCTTGCAT 4680
GATCCAGCTCATCGGGTTTGAGGTAAGACGAATCCACAACGCTCA 4725
CAATGTTCAATACCCGATCTATAATTATCATTGGAGACTAACGCA 4770
TTTGGACAGTCTTCGCACTTAAGTAGGGGAGATTGGCGCGTTCAC 4815
CTCCTTGCAGCCAACACACTCATTCCTGTGTTGGTCGAGGGTTGG 4860
TCCACAGCTTTGCAATCAGGCCCTCCAGCCACTTCAATCTGGTGT 4905
GAGTTGGATGATTCGGATTTCGGCTCAACTGAAGATCAAAATTCC 4950
TTGAGCTTCGAATATCTTGGTGCTTTGAGATTCTTGTCAAACTCC 4995
CTGGCGACAACCGGTATCTTATCGTGCATATCTGTTGGCCCATCA 5040
GCACCATTCGAAGATTATGGTCACCTCTTAGACCAGCCAGGCCTC 5085
ATACAGATGGATGAGGTGCTAGGGTGCAAGAACTGGGCCATGCTG 5130
ACTATACTCGAAGTGGGTAAGCTGGACCGGTGGAAGCGCCAGGAG 5175
CAAGAGCACAACCGTTTGAGCCTAAAGACACTCGCTAGGCGTGCA 5220
ATGATGATAGAGGACATGTTGACAGACGAGCTACAAAAGCTTCCG 5265
GCAAGCGAGACACTGCCTGATCTCATCAACCATATTTACGCCGCC 5310
TCCATTATGACATACCTGCATACAGTAGTTTCAGGACTCAATCCC 5355
AACCTTTCAGAGGTCCAGGATAGTGTGAACGCAACGATTCTATTG 5400
TTGGAGAGACTCCCAGATCTGCAAGCTGTCGCGTCTGTTACTTGG 5445
CCTTTGGCTGTCACAGGTTGCATGGCCTCGGAAAGTCATAAGGAC 5490
TTTTTCAGAAATACTCTGAGGTCCTATGACGCGACATTCACCTCG 5535
TTAAAAAAGTATGATGGAACTCTTGAGGTTTTGGAAGACGCTTGG 5580
AACAAACGAGAGATAGACAGAGAGTCTCCAATCAGGTGGGAGGAT 5625
CTGATGGATCACCATGGGCTTCCAGTGCTCCTACTCTAGGGTTGG 5670
TATCATCCCCAGACACTCGTGCTACCAACACAGAGACTGTCTTTA 5715
GTCTTTATTTTGCATACGCTACCTGATTCATGTAAGTTCGGTGTT 5760
CACTTGCCGACGATACATCCAGGGAAGTCTGACTAGTCAGTGCTT 5805
ATGGTTCGATTCCTTTTGGCGTTATAAACCGGTTCTGTCATGAAG 5850
CAAGATATGATTTCGATGAGAGGGAAGAGCGAACAACTATTCACA 5895
TGTAACTTAAATTATAGACTTTCAGTATAAACTTTCGATTATAAG 5940
```

Fig. 2D

```
CCACACCTAATCTAAGTATATATATCCAATCAATTGTACCAAAAG 5985
TAGTCTGGAATCATGGTTGTCAATCGGTGCTGTGTTCCTCCATAT 6030
TCTTGACATGATTTGACTTGTCCGGTCCGCGCGACACACGATGTT 6075
GATCATAATGAAGGAGTGTTGATTTTGAGTAGGAAAAGATATTGC 6120
AGTTCCTTGTAAAGATCGTTCGGAACGAAACCCGGCTGGAGTATG 6165
ATTTGTTCGTGGACCCGAAGTGCAAAAATGCCGGAATTAATGACA 6210
GGCATTCTCTTCAGTTGGCTTGGGTTGAGATATTGGTCTGCGTCT 6255
GTTGGAAAGCTGACATTGGATCTTCAACATGCTTTTGCCGCGACC 6300
CAGATGGTTGCGCATAAGGCAGCGCTGACTCCCGAGTATGCGAAA 6345
ACCTCGAGCCACGAAACATCAGGGTCCATTTCCGTTGAGTCGATC 6390
AATTTAGCGGCTGCGAGCATCTTGAGAGTTTTGGGATAAGTCTTT 6435
GAGTGGACAACAGTAATGTGATATGGTATGATCTGATGTCGTGTT 6480
CGTGTTGATGAGAATAAATTGTTGAGCTGATTCCCATCGGCTCTG 6525
ACCAACAGTTAATATCTAAATTCTTCTACTATCTATGCACTATGG 6570
ACTGGGGAGTCAACGTTGTTCGTTCTCTGGAGAGAGGCCTAAATG 6615
ATCTTGAATTGGTGTGTAACTGAAACGTCAGTAGAAGGCCTGAAT 6660
TCGCAAGCGCCGAACTTCCGGCCTACACTGCCACTGACTTTGCGG 6705
CTCAGCATTTAGATAGTGGGCTTCACAGCGGGTATTGTCTCTTCT 6750
GCAGCATTGCTACGGATTTATCGGCTTCAACAACCCTTGCTGAAC 6795
CAATGATGGGTTACATTGATGGGCATTCGTTTTTAAACTTTTGTC 6840
AGGTTGGCAGAGGCCTAAAATCTGCCGTCGGTGTGTGAGAGACCA 6885
TGAATCAGGCCCCTGCATTAATGTAGGGCATTTGCTAGCCCGCGG 6930
CAAGAGCGCAGAAAGC 6946
```

Fig. 2E

**Wild type *tri5* region**
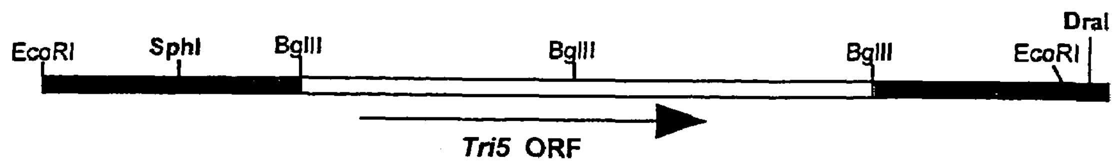
***tri5* deletion and replacement with the *amdS* marker**
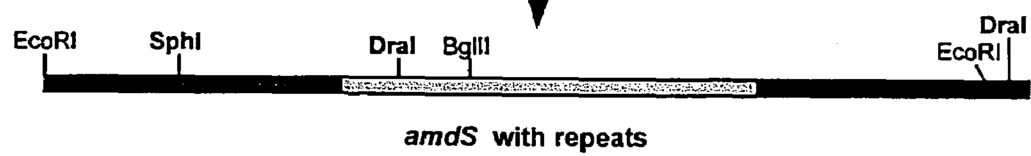
***amdS* loop-out**
EcoRI SphI DraI EcoRI
deletion with single repeat
Fig. 9

METHODS FOR PRODUCING HETEROLOGOUS POLYPEPTIDES IN TRICHOTHECENE-DEFICIENT FILAMENTOUS FUNGAL MUTANT CELLS

CROSS-REFERENCE TO RELATED APPLICATIONS

This application is a divisional of U.S. application Ser. No. 09/316,080 filed May 20, 1999, now U.S. Pat. No. 6,180,366, which is a continuation-in-part of U.S. application Ser. No. 09/082,217 filed May 20, 1998, now abandoned, which applications are fully incorporated herein by reference.

BACKGROUND OF THE INVENTION

1. Field of the Invention

The present invention relates to methods for producing heterologous polypeptides in trichothecene-deficient filamentous fungal mutant cells. The present invention also relates to such mutant cells of filamentous fungal cells and methods for obtaining the mutant cells. The present invention also relates to isolated trichodiene synthases and isolated nucleic acid sequences encoding the trichodiene synthases. The present invention also relates to nucleic acid constructs, vectors, and host cells comprising the nucleic acid sequences as well as methods for producing the trichodiene synthases. The present invention further relates to mutants cells comprising a marker-free modification of a gene, and methods for obtaining and using such mutant cells.

2. Description of the Related Art

Trichothecenes are sesquiterpene epoxides which are named after the fungus *Trichothecium roseum* from which the first trichothecene was isolated. The trichothecenes T-2 toxin, diacetoxyscirpenol, and deoxynivalenol are most commonly found in agricultural commodities infected with *Fusarium* species. Interest in these compounds is due primarily to the discovery that trichothecene contamination of foods and feeds may be detrimental in humans and animals.

Trichothecenes are produced by a sequence of oxygenations, isomerizations, cyclizations, and esterifications leading from trichodiene, which is produced from the cyclization of trans, trans-farnesyl pyrophosphate by the enzyme trichodiene synthase (Desjardins, Hohn, and McCormick, 1993, *Microbiological Reviews* 57: 595-604).

The trichodiene synthase gene (tri5 or tox5) has been cloned from *Fusarium sporotrichioides* (Hohn and Beremand, 1989, *Gene* 79: 131-138); *Gibberella pulicaris* (Hohn and Desjardins, 1992, *Molecular Plant-Microbe Interactions* 5: 249-256); *Gibberella zeae* (Proctor et al., 1995, *Molecular Plant-Microbe Interactions* 4: 593-601); *Myrothecium roridin* (Trapp, et al., 1995, *Journal of Cellular Biochemistry Supplement* 19B: 154); and *Fusarium poae* (Fekete et al., 1997, *Mycopathologia* 138: 91-97).

Tri5 mutants of *Gibberella pulicaris* (Hohn and Desjardins, 1992, supra) and *Gibberella zeae* (Proctor et al., 1995, supra) have been generated which do not produce trichothecenes.

Other genes in the trichothecene biosynthetic pathway have been cloned including the tri3 gene, encoding a 15-O-acetyltransferase, from *Fusarium sporotrichioides* (McCormick et al., 1996, *Applied and Environmental Microbiology* 62: 353-359); the tri4 gene, encoding a cytochrome P450 monooxygenase, from *Fusarium sporotrichioides* (Hohn et al., 1995, *Molecular and General Genetics* 248: 95-102); the tri6 gene, encoding a zinc finger protein involved in the regulation of trichothecene biosynthesis, from *Fusarium sporotrichioides* (Proctor et al., 1995, *Applied and Environmental Microbiology* 61: 1923-1930); the trill gene, encoding a cytochrome P450 monooxygenase required for C-15 hydroxylation, from *Fusarium sporotrichioides* (Alexander et al., 1997, *Applied and Environmental Microbiology* 64: 221-225); the tri12 gene, which encodes an apparent transport protein involved in trichothecene production, from *Fusarium sporotrichioides* (Alexander et al., 1997, *Cereal Research Communications* 25: 347-348); and the tri101 gene, encoding a 3-O-acetyltransferase, from *Fusarium graminearum* (Kimura et al., 1998, *Journal of Biological Chemistry* 272: 1654-1661).

It is an object of the present invention to provide methods for producing polypeptides in mutant cells.

SUMMARY OF THE INVENTION

The present invention relates to methods for producing a heterologous polypeptide, comprising: (a) cultivating a mutant cell of a parent filamentous fungal cell under conditions conducive for the production of the heterologous polypeptide, wherein (i) the mutant cell comprises a first nucleic acid sequence encoding the heterologous polypeptide and a second nucleic acid sequence comprising a modification of at least one of the genes involved in the production of a trichothecene and (ii) the mutant cell produces less of the trichothecene than the parent filamentous fungal cell when cultured under the same conditions; and (b) isolating the heterologous polypeptide from the cultivation medium. The present invention also relates to mutant cells of filamentous fungal cells and methods for obtaining the mutant cells.

The present invention also relates to isolated trichodiene synthases and isolated nucleic acid sequences encoding the trichodiene synthases. The invention further relates to nucleic acid constructs, vectors, and host cells comprising the nucleic acid sequences as well as methods for producing the trichodiene synthases.

The present invention also relates to methods for obtaining a mutant cell, comprising: (a) introducing into a parent cell, having a first nucleic acid sequence encoding a first polypeptide, a first nucleic acid construct comprising a nitrate reductase gene as a selectable marker and a modification of the first nucleic acid sequence, wherein the first construct incorporates into the genome of the parent cell replacing the endogenous first nucleic acid sequence with the modified first nucleic acid sequence resulting in reduced production of the first polypeptide compared to the parent cell when cultivated under the same conditions; and (b) selecting a mutant cell from step (a) for the presence of the nitrate reductase gene and reduced production of the first polypeptide.

In a preferred embodiment, the methods for obtaining a mutant cell may further comprise (c) selecting a mutant cell from step (b) under culturing conditions in which the nitrate reductase gene is deleted. In another preferred embodiment, the methods for obtaining a mutant cell may further comprise (c) introducing into the mutant cell from step (b) a second nucleic acid construct comprising a second nucleic acid sequence comprising 5' and 3' regions of the modified first nucleic acid sequence, but lacking the nitrate reductase gene, wherein the second construct incorporates into the genome of the parent cell replacing the modified first nucleic acid sequence with the second nucleic acid sequence; and (d) selecting a mutant cell from step (c) under culturing conditions in which the nitrate reductase gene is deleted.

The present invention further relates to mutant cells obtained from such methods and methods for producing polypeptides with such mutant cells.

BRIEF DESCRIPTION OF FIGURES

FIGS. 2A-2E shows the genomic nucleic acid sequence and the deduced amino acid sequence of a *Fusarium venenatum* ATCC 20334 trichodiene synthase (SEQ ID NOS. 1 and 2, respectively).

FIG. 9 shows the protocol for deletion of the tri5 gene and removal of the amdS selectable marker.

DETAILED DESCRIPTION OF THE INVENTION

Trichothecene-Deficeint Mutant Cells

The present invention relates to methods for producing a heterologous polypeptide, comprising: (a) cultivating a mutant cell of a parent filamentous fungal cell under conditions conducive for the production of the heterologous polypeptide, wherein (i) the mutant cell relates to the parent cell by a modification, e.g., disruption or deletion, of one or more genes involved in the production of a trichothecene and (ii) the mutant cell produces less of the trichothecene than the parent cell when cultured under the same conditions; and (b) isolating the heterologous polypeptide from the cultivation medium of the mutant cell.

Figure 1:
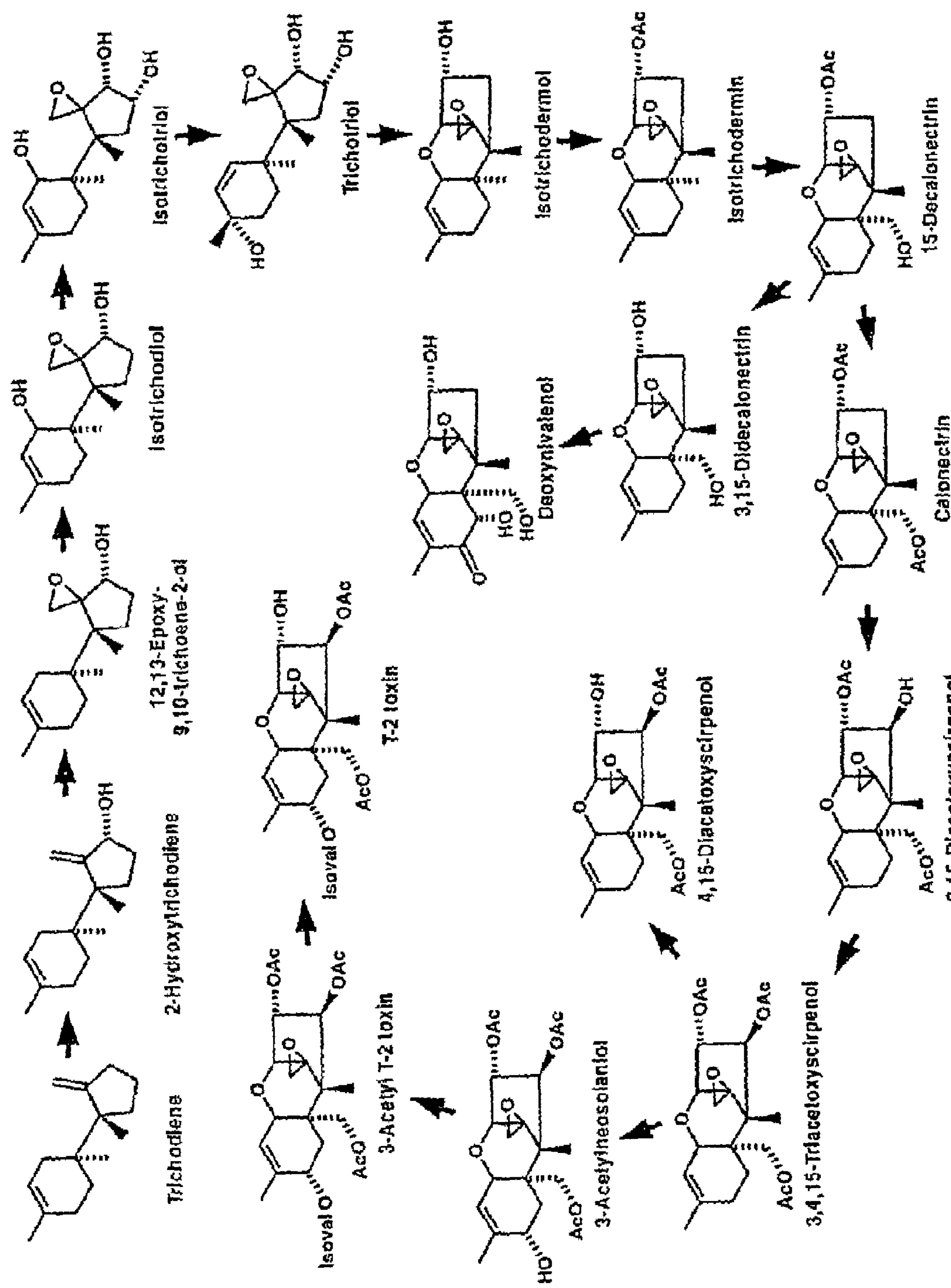
FIG. 1 shows the trichothecene biosynthetic pathway in *Fusarium* species.

The term "trichothecenes" is defined herein as a family of sesquiterpene epoxides produced by a sequence of oxygenations, isomerizations, cyclizations, and esterifications leading from trichodiene to the more complex trichothecenes. The trichothecenes include, but are not limited to, 2-hydroxytrichodiene, 12,13-epoxy-9,10-trichoene-2-ol, isotrichodiol, isotrichotriol, trichotriol, isotrichodermol, isotrichodermin, 15-decalonectrin, 3,15-didecalonectrin, deoxynivalenol, 3-acetyldeoxynivalenol, calonectrin, 3,15-diacetoxyscirpenol, 3,4,15-triacetoxyscirpenol, 4,15-diacetoxyscirpenol, 3-acetylneosolaniol, acetyl T-2 toxin, and T-2 toxin; and derivatives thereof. The trichothecene biosynthetic pathway is shown in FIG. 1 (Desjardins, Hohn, and McCormick, 1993, supra).

The term "production of a trichothecene" is defined herein to include any step involved in the production of a trichothecene including, but not limited to, biosynthesis, regulation of biosynthesis, transport, and secretion.

In the methods of the present invention, the filamentous fungal cell may be a wild-type cell or a mutant thereof. Furthermore, the filamentous fungal cell may be a cell which does not produce any detectable trichothecene(s), but contains the genes encoding a trichothecene(s). Preferably, the filamentous fungal cell is an *Acremonium, Aspergillus, Aureobasidium, Cryptococcus, Filibasidium, Fusarium, Gibberella, Humicola, Magnaporthe, Mucor, Myceliophthora, Myrothecium, Neocallimastix, Neurospora, Paecilomyces, Penicillium, Piromyces, Schizophyllum, Talaromyces, Thermoascus, Thielavia, Tolypocladium*, or *Trichoderma cell.*

In a preferred embodiment, the filamentous fungal cell is an *Aspergillus aculeatus, Aspergillus awamori, Aspergillus foetidus, Aspergillus japonicus, Aspergillus nidulans, Aspergillus niger*, or *Aspergillus oryzae* cell.

In another preferred embodiment, the filamentous fungal cell is a *Fusarium bactridioides, Fusarium crookwellense* (synonym of *Fusarium cerealis*), *Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium solani, Fusarium sporotrichioides, Fusarium sulphureum, Fusarium torulosum, Fusarium trichothecioides*, or *Fusarium venenatum* cell.

In another preferred embodiment, the filamentous fungal cell is a *Gibberella pulicaris, Gibberella zeae, Humicola insolens, Humicola lanuginosa, Mucor miehei, Myceliophthora thermophila, Myrothecium roridin, Neurospora crassa*, or *Penicillium purpurogenum* cell.

In another preferred embodiment, the filamentous fungal cell is a *Trichoderma harzianum, Trichoderma koningii, Trichoderma longibrachiatum, Trichoderma reesei*, or *Trichoderma viride* cell.

In a more preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62-80 and O'Donnell et al., 1998, *Fungal Genetics and Biology* 23: 57-67; as well as taxonomic equivalents of *Fusarium venenatum* regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

In the methods of the present invention, any gene of a filamentous fungal cell involved in the production of a trichothecene may be modified including, but not limited to, tri3, tri4, tri5, tri6, tri11, tri12, and/or tri101. In a preferred embodiment, the gene is tri5. In a more preferred embodiment, the gene is the *Fusarium venenatum* tri5 gene having the nucleic acid sequence of SEQ ID NO. 1.

The trichothecene-deficient filamentous fungal mutant cell may be constructed by reducing or eliminating expression of one or more of the genes described herein using methods well known in the art, for example, insertions, disruptions, replacements, or deletions. The gene to be modified or inactivated may be, for example, the coding region or a part thereof essential for activity, or the gene may contain a regulatory element required for expression of the coding region. An example of such a regulatory or control sequence may be a promoter sequence or a functional part thereof, i.e., a part which is sufficient for affecting expression of the nucleic acid sequence. Other control sequences for possible modification include, but are not limited to, a leader, polyadenylation sequence, propeptide sequence, signal sequence, transcription terminator, and transcriptional activator.

Modification or inactivation of the gene may be performed by subjecting the parent cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues.

When such agents are used, the mutagenesis is typically performed by incubating the parent cell to be mutagenized in the presence of the mutagenizing agent of choice under suitable conditions, and selecting for mutant cells exhibiting reduced or no expression of the gene.

Modification or inactivation of the gene may be also accomplished by introduction, substitution, or removal of one or more nucleotides in the gene or a regulatory element required for the transcription or translation thereof. For example, nucleotides may be inserted or removed so as to result in the introduction of a stop codon, the removal of the start codon, or a change of the open reading frame. Such a modification or inactivation may be accomplished by site-directed mutagenesis or PCR generated mutagenesis in accordance with methods known in the art. Although, in principle, the modification may be performed in vivo, i.e., directly on the cell expressing the gene to be modified, it is preferred that the modification be performed in vitro as exemplified below.

An example of a convenient way to inactivate or reduce production of a trichothecene by a filamentous fungal cell of choice is based on techniques of gene replacement, gene deletion, or gene disruption. For example, in the gene disruption method, a nucleic acid sequence corresponding to the endogenous gene or gene fragment of interest is mutagenized in vitro to produce a defective nucleic acid sequence which is then transformed into the parent cell to produce a defective gene. By homologous recombination, the defective nucleic acid sequence replaces the endogenous gene or gene fragment. It may be desirable that the defective gene or gene fragment also encodes a marker which may be used for selection of transformants in which the nucleic acid sequence has been modified or destroyed. The selectable marker gene may be used to achieve the disruption. The defective nucleic acid sequence may be a simple disruption of the endogenous sequence with a selectable marker gene. Alternatively, the defective nucleic acid sequence may contain an insertion or deletion of the endogenous sequence, or a portion thereof, in addition to the disruption with the selectable marker gene. Furthermore, the defective nucleic acid sequence may contain an insertion or deletion of the endogenous sequence, or a portion thereof, and the selectable marker gene is not involved in the modification but is used as a selectable marker for identifying transformants containing the defective gene.

Alternatively, modification or inactivation of the gene may be performed by established anti-sense techniques using a nucleotide sequence complementary to the nucleic acid sequence of the gene. More specifically, expression of the gene by a filamentous fungal cell may be reduced or eliminated by introducing a nucleotide sequence complementary to the nucleic acid sequence of the gene which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated.

A nucleic acid sequence homologous or complementary to the nucleic acid sequence of a gene involved in the production of a trichothecene in a filamentous fungal cell may be obtained from other microbial sources which produce trichothecenes. Preferred sources for a tri5 gene having a nucleic acid sequence complementary or homologous to the nucleic acid sequence of SEQ ID NO. 1 of *Fusarium venenatum* include, but are not limited to, *Fusarium sporotrichioides* (Hohn and Beremand, 1989, supra); *Gibberella pulicaris* (Hohn and Desjardins, 1992, supra); *Gibberella zeae* (Proctor et al., 1995, supra); *Myrothecium roridin* (Trapp et al., 1995, supra); and *Fusarium poae* (Fekete et al., 1997, supra).

Preferred sources for other genes in the trichothecene biosynthetic pathway which may be complementary or homologous to the nucleic acid sequence of the corresponding genes of a filamentous fungal cell include, but are not limited to, the tri3 gene from *Fusarium sporotrichioides* (McCormick et al., 1996, supra); the tri4 gene from *Fusarium sporotrichioides* (Hohn et al., 1995, supra); the tri6 gene from *Fusarium sporotrichioides* (Proctor et al., 1995, supra); the tri11 gene from *Fusarium sporotrichioides* (Alexander et al., 1997, supra); the tri12 gene from *Fusarium sporotrichioides* (Alexander et al., 1997, supra); and the tri101 gene from *Fusarium graminearum* (Kimura et al., 1998, supra). Furthermore, the nucleic acid sequences may be native to the filamentous fungal cell.

In a preferred embodiment, the modification of a gene involved in the production of a trichothecene in the mutant filamentous fungal cell is unmarked with a selectable marker.

Removal of the selectable marker gene may be selected for by culturing the mutants on a counter-selection medium. Where the selectable marker gene contains repeats flanking its 5' and 3' ends, the repeats will facilitate the looping out of the selectable marker gene by homologous recombination when the mutant cell is submitted to counter-selection. The selectable marker gene may also be removed by homologous recombination by introducing into the mutant cell a nucleic acid fragment comprising 5' and 3' regions of the defective gene, but lacking the selectable marker gene, followed by selecting on the counter-selection medium. By homologous recombination, the defective gene containing the selectable marker gene is replaced with the nucleic acid fragment lacking the selectable marker gene. Other methods known in the art may also be used.

It will be understood that the methods of the present invention are not limited to a particular order for obtaining the mutant filamentous fungal cell. The modification of the gene involved in the production of a trichothecene may be introduced into the parent cell at any step in the construction of the cell for the production of a heterologous polypeptide. It is preferable that the filamentous fungal mutant has already been made trichothecene-deficient prior to the introduction of a gene encoding a heterologous polypeptide.

The level of trichothecenes produced by a mutant filamentous fungal cell of the present invention may be determined using methods well known in the art (see, for example, Rood et al., 1988, *Journal of Agricultural and Food Chemistry* 36:74-79; Romer, 1986, *Journal of the Association of Official Analytical Chemists* 69: 699-703; McCormick et al., 1990, *Applied and Environmental Microbiology* 56: 702-706). The mutant filamentous fungal cell preferably produces at least about 25% less, more preferably at least about 50% less, even more preferably at least about 75% less, most preferably at least about 95% less, and even most preferably no trichothecene compared to the corresponding parent filamentous fungal cell when cultured under identical conditions. The parent and mutant cells may be compared with regard to production of a trichothecene under conditions conducive for the production of a polypeptide of interest or under conditions conducive for the production of a trichothecene.

The mutant filamentous fungal cell is cultivated in a nutrient medium suitable for production of a heterologous polypeptide of interest using methods known in the art. For example, the cell may be cultivated by shake flask cultivation, or small-scale or large-scale fermentation (including continuous, batch, fed-batch, or solid state fermentations) in laboratory or industrial fermentors with a suitable medium and under conditions allowing the heterologous polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). The heterologous polypeptide can be recovered directly from the medium if secreted.

The heterologous polypeptide may be detected using methods known in the art that are specific for the polypeptide. These detection methods may include use of specific antibodies, formation of an enzyme product, disappearance of an enzyme substrate, SDS-PAGE, or any other method known in the art. For example, an enzyme assay may be used to determine the activity of the heterologous polypeptide. Procedures for determining enzyme activity are known in the art for many enzymes.

The resulting heterologous polypeptide may be isolated by methods known in the art. For example, the polypeptide may be isolated from the nutrient medium by conventional procedures including, but not limited to, centrifugation, filtration, extraction, spray-drying, evaporation, or precipitation. The isolated polypeptide may then be further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), or extraction (see, e.g., *Protein Purification*, J.-C. Janson and Lars Ryden, editors, VCH Publishers, New York, 1989).

The polypeptide may be any polypeptide heterologous to the mutant filamentous fungal cell. The term "polypeptide" is not meant herein to refer to a specific length of the encoded product and, therefore, encompasses peptides, oligopeptides, and proteins. The term "heterologous polypeptide" is defined herein as a polypeptide which is not native to the filamentous fungal cell. The mutant filamentous fungal cell may contain one or more copies of the nucleic acid sequence encoding the heterologous polypeptide.

In a preferred embodiment, the heterologous polypeptide is a hormone, hormone variant, enzyme, receptor or portion thereof, antibody or portion thereof, or reporter. In a more preferred embodiment, the heterologous polypeptide is an oxidoreductase, transferase, hydrolase, lyase, isomerase, or ligase. In an even more preferred embodiment, the heterologous polypeptide is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase or xylanase.

In the methods of the present invention, the heterologous polypeptide may also be an engineered variant of a polypeptide.

The nucleic acid sequence encoding a heterologous polypeptide which can be expressed in a filamentous fungal cell may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

In the methods of the present invention, the mutant filamentous fungal cell may also be used for the recombinant production of polypeptides which are native to the cell. The native polypeptides may be recombinantly produced by, for example, placing a gene encoding the polypeptide under the control of a different promoter to enhance expression of the polypeptide, to expedite export of a native polypeptide of interest outside the cell by use of a signal sequence, and to increase the copy number of a gene encoding the polypeptide normally produced by the cell. The present invention also encompasses, within the scope of the term "heterologous polypeptide", such recombinant production of endogenous polypeptides native to the filamentous fungal cell, to the extent that such expression involves the use of genetic elements not native to the cell, or use of native elements which have been manipulated to function in a manner that do not normally occur in the host cell.

The techniques used to isolate or clone a nucleic acid sequence encoding a heterologous polypeptide are known in the art and include isolation from genomic DNA, preparation from cDNA, or a combination thereof. The cloning of the nucleic acid sequence from such genomic DNA can be effected, e.g., by using the well known polymerase chain reaction (PCR). See, for example, Innis et al., 1990, *PCR Protocols: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The cloning procedures may involve excision and isolation of a desired nucleic acid fragment comprising the nucleic acid sequence encoding the polypeptide, insertion of the fragment into a vector molecule, and incorporation of the recombinant vector into the mutant fungal cell where multiple copies or clones of the nucleic acid sequence will be replicated. The nucleic acid sequence may be of genomic, cDNA, RNA, semisynthetic, synthetic origin, or any combinations thereof.

In the methods of the present invention, heterologous polypeptides may also include fused or hybrid polypeptides in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptides may comprise a combination of partial or complete polypeptide sequences obtained from at least two different polypeptides wherein one or more may be heterologous to the mutant filamentous fungal cell.

An isolated nucleic acid sequence encoding a heterologous polypeptide of interest may be manipulated in a variety of ways to provide for expression of the polypeptide. Expression will be understood to include any step involved in the production of the polypeptide including, but not limited to, transcription, post-transcriptional modification, translation, post-translational modification, and secretion. Manipulation of the nucleic acid sequence prior to its insertion into a vector may be desirable or necessary depending on the expression vector. The techniques for modifying nucleic acid sequences utilizing cloning methods are well known in the art.

"Nucleic acid construct" is defined herein as a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term expression cassette when the nucleic acid construct contains all the control sequences required for expression of a coding sequence. The term "coding sequence" as defined herein is a sequence which is transcribed into mRNA and translated into a polypeptide. The boundaries of the genomic coding sequence are generally determined by the ATG start codon located just upstream of the open reading frame at the 5' end of the mRNA and a transcription terminator sequence located just downstream of the open reading frame at the 3' end of the mRNA. A coding sequence can include, but is not limited to, genomic, cDNA, RNA, semisynthetic, synthetic, recombinant, or any combinations thereof.

The term "control sequences" is defined herein to include all components which are necessary or advantageous for the expression of a heterologous polypeptide. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a heterologous polypeptide. The term "operably linked" is defined herein as a configuration in which a control sequence is appropriately placed at a position relative to the coding sequence of the DNA sequence such that the control sequence directs the production of a heterologous polypeptide.

The control sequence may be an appropriate promoter sequence, a nucleic acid sequence which is recognized by a filamentous fungal cell for expression of the nucleic acid sequence. The promoter sequence contains transcriptional control sequences which mediate the expression of the heterologous polypeptide. The promoter may be any nucleic acid sequence which shows transcriptional activity in the filamentous fungal cell including mutant, truncated, and hybrid promoters, and may be obtained from genes encoding extracellular or intracellular polypeptides either homologous or heterologous to the cell.

Examples of suitable promoters for directing the transcription of the nucleic acid constructs in the methods of the present invention are promoters obtained from the genes encoding *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Aspergillus oryzae* acetamidase, *Fusarium oxysporum* trypsin-like protease (U.S. Pat. No. 4,288,627), and mutant, truncated, and hybrid promoters thereof. Particularly preferred promoters are the glucoamylase, TAKA amylase, and NA2-tpi promoters (a hybrid of the promoters from the genes encoding *Aspergillus niger* neutral alpha-amylase and *Aspergillus oryzae* triose phosphate isomerase).

The control sequence may also be a suitable transcription terminator sequence, a sequence recognized by a filamentous fungal cell to terminate transcription. The terminator sequence is operably linked to the 3' terminus of the nucleic acid sequence encoding the heterologous polypeptide. Any terminator which is functional in the filamentous fungal cell may be used in the present invention.

Preferred terminators are obtained from the genes encoding *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

The control sequence may also be a suitable leader sequence, a nontranslated region of a mRNA which is important for translation by the filamentous fungal cell. The leader sequence is operably linked to the 5' terminus of the nucleic acid sequence encoding the heterologous polypeptide. Any leader sequence which is functional in the filamentous fungal cell may be used in the present invention.

Preferred leaders are obtained from the genes encoding *Aspergillus oryzae* TAKA amylase and *Aspergillus nidulans* triose phosphate isomerase.

The control sequence may also be a polyadenylation sequence, a sequence which is operably linked to the 3' terminus of the nucleic acid sequence and which, when transcribed, is recognized by a filamentous fungal cell as a signal to add polyadenosine residues to transcribed mRNA. Any polyadenylation sequence which is functional in the filamentous fungal cell may be used in the present invention.

Preferred polyadenylation sequences are obtained from the genes encoding *Aspergillus oryzae* TAKA amylase, *Aspergillus niger* glucoamylase, *Aspergillus nidulans* anthranilate synthase, and *Aspergillus niger* alpha-glucosidase.

The control sequence may also be a signal peptide coding region that codes for an amino acid sequence linked to the amino terminus of the heterologous polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not normally contain a signal peptide coding region. Alternatively, the foreign signal peptide coding region may simply replace the natural signal peptide coding region in order to obtain enhanced secretion of the polypeptide. However, any signal peptide coding region which directs the expressed heterologous polypeptide into the secretory pathway of a filamentous fungal cell may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

The control sequence may also be a propeptide coding region, which codes for an amino acid sequence positioned at the amino terminus of a polypeptide. The resultant polypeptide is known as a proenzyme or propolypeptide (or a zymogen in some cases). A propolypeptide is generally inactive and can be converted to a mature, active polypeptide by catalytic or autocatalytic cleavage of the propeptide from the propolypeptide. The propeptide coding region may be obtained from the Rhizomucor miehei aspartic proteinase gene, or the Myceliophthora thermophila laccase gene (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

The nucleic acid constructs may also comprise one or more nucleic acid sequences which encode one or more factors that are advantageous for directing the expression of the heterologous polypeptide, e.g., a transcriptional activator (e.g., a trans-acting factor), a chaperone, and a processing protease. Any factor that is functional in a filamentous fungal cell may be used in the present invention. The nucleic acids encoding one or more of these factors are not necessarily in tandem with the nucleic acid sequence encoding the heterologous polypeptide.

It may also be desirable to add regulatory sequences which allow the regulation of the expression of the heterologous polypeptide relative to the growth of the filamentous fungal cell. Examples of regulatory systems are those which cause the expression of the gene to be turned on or off in response to a chemical or physical stimulus, including the presence of a regulatory compound. The TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification, e.g., the metallothionein genes which are amplified with heavy metals. In these cases, the nucleic acid sequence encoding the heterologous polypeptide would be operably linked with the regulatory sequence.

The expression of a nucleic acid sequence which is endogenous to a cell may also be altered using a nucleic acid construct containing the minimal number of components necessary for altering expression of the endogenous nucleic acid sequence. In one embodiment, the nucleic acid constructs preferably contain (a) a targeting sequence, (b) a regulatory sequence, (c) an exon, and (d) a splice-donor site. Upon introduction of the nucleic acid construct into a cell, the construct inserts by homologous recombination into the cellular genome at the endogenous nucleic acid sequence site. The targeting sequence directs the integration of elements (a)-(d) into the endogenous nucleic acid sequence such that elements (b)-(d) are operably linked to the endogenous nucleic acid sequence. In another embodiment, the nucleic acid constructs contain (a) a targeting sequence, (b) a regulatory sequence, (c) an exon, (d) a splice-donor site, (e) an intron, and (f) a splice-acceptor site, wherein the targeting sequence directs the integration of elements (a)-(f) such that elements (b)-(f) are operably linked to the endogenous nucleic acid sequence. However, the constructs may contain additional components such as a selectable marker.

In both embodiments, the introduction of these components results in production of a new transcription unit in which expression of the endogenous nucleic acid sequence is altered. In essence, the new transcription unit is a fusion product of the sequences introduced by the targeting constructs and the endogenous nucleic acid sequence. In one embodiment, in which the endogenous nucleic acid sequence is altered, the nucleic acid sequence is activated. In this embodiment, homologous recombination is used to replace, disrupt, or disable the regulatory region normally associated with the endogenous nucleic acid sequence of a parent cell through the insertion of a regulatory sequence which causes the nucleic acid sequence to be expressed at higher levels than evident in the corresponding parent cell. The activated nucleic acid sequence can be further amplified by the inclusion of an amplifiable selectable marker gene in the construct using methods well known in the art (see, for example, U.S. Pat. No. 5,641,670). In another embodiment, in which the endogenous nucleic acid sequence is altered, expression of the gene is reduced.

The targeting sequence can be within the endogenous nucleic acid sequence, immediately adjacent to the nucleic acid sequence, within an upstream gene, or upstream of and at a distance from the endogenous nucleic acid sequence. One or more targeting sequences can be used. For example, a circular plasmid or DNA fragment thereof preferably employs a single targeting sequence, while a linear plasmid or DNA fragment thereof preferably employs two targeting sequences.

The regulatory sequence of the construct can be comprised of one or more promoters, enhancers, scaffold-attachment regions or matrix attachment sites, negative regulatory elements, transcription binding sites, or combinations of these sequences.

The constructs further contain one or more exons of the endogenous nucleic acid sequence. An exon is defined as a DNA sequence which is copied into RNA and is present in a mature mRNA molecule such that the exon sequence is in-frame with the coding region of the endogenous nucleic acid sequence. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous nucleic acid sequence so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

The various nucleic acid and control sequences described above may be joined together to produce a recombinant expression vector which may include one or more convenient restriction sites to allow for insertion or substitution of the nucleic acid sequence encoding the heterologous polypeptide at such sites. Alternatively, the nucleic acid sequence encoding the heterologous polypeptide may be expressed by inserting the sequence or a nucleic acid construct comprising the sequence into an appropriate vector for expression. In creating the expression vector, the coding sequence is located in the vector so that the coding sequence is operably linked with the appropriate control sequences for expression, and possibly secretion.

The recombinant expression vector may be any vector (e.g., a plasmid or virus) which can be conveniently subjected to recombinant DNA procedures and can bring about the expression of the nucleic acid sequence encoding the heterologous polypeptide. The choice of the vector will typically depend on the compatibility of the vector with the filamentous fungal cell into which the vector is to be introduced. The vectors may be linear or closed circular plasmids. The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the filamentous fungal cell, is integrated into the genome and replicated together with the chromosome(s) into which it has been integrated. The vector system may be a single vector or plasmid or two or more vectors or plasmids which together contain the total DNA to be introduced into the genome of the filamentous fungal cell, or a transposon.

The vectors preferably contain one or more selectable markers which permit easy selection of transformed filamentous fungal cells. A selectable marker is a gene the product of which provides for biocide or viral resistance, resistance to heavy metals, prototrophy to auxotrophs, and the like. A selectable marker for use in a filamentous fungal host cell may be selected from the group including, but not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents from other species. Preferred for use in a filamentous fungal cell are the amdS and pyrG genes of *Aspergillus nidulans* or *Aspergillus oryzae* and the bar gene of *Streptomyces hygroscopicus.*

The vectors preferably contain an element(s) that permits stable integration of the vector into a filamentous fungal cell genome or autonomous replication of the vector in the cell independent of the genome of the cell.

"Introduction" means introducing a vector comprising the nucleic acid sequence into a filamentous fungal cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the chromosome occurs by homologous recombination, non-homologous recombination, or transposition.

The introduction of an expression vector into a filamentous fungal cell may involve a process consisting of protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods of transforming *Fusarium* species are described by Malardier et al., 1989, *Gene* 78: 147-156, and WO 96/00787.

For integration into the genome of a filamentous fungal cell, the vector may rely on the nucleic acid sequence encoding the heterologous polypeptide or any other element of the vector for stable integration of the vector into the genome by homologous or nonhomologous recombination. Alternatively, the vector may contain additional nucleic acid sequences for directing integration by homologous recombination into the genome of the filamentous fungal cell. The additional nucleic acid sequences enable the vector to be integrated into the genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequences that are homologous with the target sequence in the genome of the filamentous fungal cell. Furthermore, the integrational elements may be non-encoding or encoding nucleic acid sequences. On the other hand, the vector may be integrated into the genome of the cell by non-homologous recombination.

For autonomous replication, the vector may further comprise an origin of replication enabling the vector to replicate autonomously in the filamentous fungal cell in question.

The procedures used to ligate the elements described herein to construct the recombinant expression vectors are well known to one skilled in the art (see, e.g., J. Sambrook, E. F. Fritsch, and T. Maniatus, 1989, *Molecular Cloning, A Laboratory Manual,* 2d edition, Cold Spring Harbor, N.Y.).

In another aspect of the present invention, the mutant filamentous fungal cell may additionally contain modifications of one or more nucleic acid sequences which encode proteins that may be detrimental to the production, recovery, and/or application of the heterologous polypeptide of interest. The modification reduces or eliminates expression of the one or more third nucleic acid sequences resulting in a mutant cell which may produce more of the heterologous polypeptide than the mutant cell without the modification of the third nucleic acid sequence when cultured under the same conditions.

The third nucleic acid sequence may encode any protein or enzyme. For example, the enzyme may be an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, or xylanase. The third nucleic acid sequence preferably encodes a proteolytic enzyme, e.g., an aminopeptidase, carboxypeptidase, or protease.

The present invention also relates to methods for obtaining a trichothecene-deficient filamentous fungal mutant cell which comprise (a) introducing into a parent filamentous fungal cell a nucleic acid sequence comprising a modification of at least one of the genes involved in the production of a trichothecene; and (b) identifying the mutant from step (a) comprising the modified nucleic acid sequence, wherein the mutant cell produces less of the trichothecene than the parent filamentous fungal cell of the mutant cell when cultured under the same conditions.

The present invention also relates to trichothecene-deficient mutants of filamentous fungal cells for producing a heterologous polypeptide which comprise a first nucleic acid sequence encoding the heterologous polypeptide and a second nucleic acid sequence comprising a modification of at least one of the genes involved in the production of a trichothecene, wherein the mutant cell produces less of the trichothecene than the parent filamentous fungal cell of the mutant cell when cultured under the same conditions.

Trichodiene Synthases and Nucleic Acids Encoding Same

The present invention also relates to isolated trichodiene synthases.

In a first embodiment, the present invention relates to isolated trichodiene synthases having an amino acid sequence which has a degree of identity to SEQ ID NO. 2 of at least about 97% (hereinafter "homologous polypeptides"). In a preferred embodiment, the homologous polypeptides have an amino acid sequence which differs by five amino acids, preferably by four amino acids, more preferably by three amino acids, even more preferably by two amino acids, and most preferably by one amino acid from SEQ ID NO. 2. For purposes of the present invention, the degree of identity between two amino acid sequences is determined by the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=1, gap penalty=3, windows=5, and diagonals=5.

Preferably, the trichodiene synthases of the present invention comprise the amino acid sequence of SEQ ID NO. 2 or an allelic variant thereof; or a fragment thereof that has trichodiene synthase activity. In a more preferred embodiment, the trichodiene synthase of the present invention comprises the amino acid sequence of SEQ ID NO. 2. In another preferred embodiment, the trichodiene synthase of the present invention consists of the amino acid sequence of SEQ ID NO. 2 or an allelic variant thereof; or a fragment thereof that has trichodiene synthase activity. In another preferred embodiment, the polypeptide of the present invention consists of the amino acid sequence of SEQ ID NO. 2.

A fragment of SEQ ID NO. 2 is a polypeptide having one or more amino acids deleted from the amino and/or carboxyl terminus of this amino acid sequence. Preferably, a fragment contains at least 290 amino acid residues, more preferably at least 320 amino acid residues, and most preferably at least 350 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

In a second embodiment, the present invention relates to isolated trichodiene synthases which are encoded by nucleic acid sequences which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with (i) nucleotides 2521 to 3686 of SEQ ID NO. 1, (ii) the cDNA sequence contained in nucleotides 2521 to 3686 of SEQ ID NO. 1, (iii) a subsequence of (i) or (ii), or (iv) a complementary strand of (i), (ii), or (iii) (J. Sambrook, E. F. Fritsch, and T. Maniatus, 1989, *Molecular Cloning, A Laboratory Manual*, 2d edition, Cold Spring Harbor, N.Y.). The subsequence of SEQ ID NO. 1 may be at least 100 nucleotides or preferably at least 200 nucleotides. Moreover, the subsequence may encode a polypeptide fragment which has trichodiene synthase activity. The polypeptides may also be allelic variants or fragments of the polypeptides that have trichodiene synthase activity.

The nucleic acid sequence of SEQ ID NO. 1 or a subsequence thereof, as well as the amino acid sequence of SEQ ID NO. 2 or a fragment thereof, may be used to design a nucleic acid probe to identify and clone DNA encoding trichodiene synthases from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}P$, $^{3}H$, $^{35}S$, biotin, avidin, fluorescein, or digoxygenin). Such probes are encompassed by the present invention.

Thus, a genomic DNA or cDNA library prepared from such other organisms may be screened for DNA which hybridizes with the probes described herein and which encodes a trichodiene synthase. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO. 1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO. 1, its complementary strand, or a subsequence thereof, under very low to very high stringency conditions. Molecules to which the nucleic acid probe hybridizes under these conditions are detected using X-ray film.

In a preferred embodiment, the nucleic acid probe is a nucleic acid sequence which encodes the polypeptide of SEQ ID NO. 2, or a subsequence thereof. In another preferred embodiment, the nucleic acid probe is SEQ ID NO. 1. In another preferred embodiment, the nucleic acid probe is nucleotides 2521 to 3686 of SEQ ID NO. 1. In another preferred embodiment, the nucleic acid probe is the nucleic acid sequence contained in plasmid pTri5 which is contained in *Escherichia coli* NRRL B-30029, wherein the nucleic acid sequence encodes a trichodiene synthase. In another preferred embodiment, the nucleic acid probe is the mature polypeptide coding region contained in plasmid pTri5 which is contained in *Escherichia coli* NRRL B-30029.

For long probes of at least 100 nucleotides in length, very low to very high stringency conditions are defined as prehybridization and hybridization at 42° C. in 5×SSPE, 0.3%

SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 2×SSC, 0.2% SDS preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes which are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1× Denhardt's solution, 1 mM sodium pyrophosphate, 1 mM sodium monobasic phosphate, 0.1 mM ATP, and 0.2 mg of yeast RNA per ml following standard Southern blotting procedures.

For short probes which are about 15 nucleotides to about 70 nucleotides in length, the carrier material is washed once in 6×SCC plus 0.1% SDS for 15 minutes and twice each for 15 minutes using 6×SSC at about 5° C. to about 10° C. below the calculated $T_m$.

In a third embodiment, the present invention relates to variants of the trichodiene synthase having an amino acid sequence of SEQ ID NO. 2 comprising a substitution, deletion, and/or insertion of one or more amino acids.

The amino acid sequences of the variant polypeptides may differ from the amino acid sequence of SEQ ID NO. 2 or the mature polypeptide thereof by an insertion or deletion of one or more amino acid residues and/or the substitution of one or more amino acid residues by different amino acid residues. Preferably, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, *In, The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

The polypeptides of the present invention have at least 20%, preferably at least 40%, more preferably at least 60%, even more preferably at least 80%, even more preferably at least 90%, and most preferably at least 100% of the trichodiene synthase activity of the mature polypeptide of SEQ ID NO. 2.

In a preferred embodiment, a trichodiene synthase of the present invention is obtained from a *Fusarium venenatum* strain, and more preferably from *Fusarium venenatum* ATCC 20334 or a mutant strain thereof, e.g., the polypeptide with the amino acid sequence of SEQ ID NO. 2.

As defined herein, an "isolated" trichodiene synthase is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

The present invention also relates to isolated nucleic acid sequences which encode a trichodiene synthase of the present invention. In a preferred embodiment, the nucleic acid sequence is set forth in SEQ ID NO.1. In another preferred embodiment, the nucleic acid sequence is the sequence contained in plasmid pTri5 that is contained in *Escherichia coli* NRRL B-30029. In another preferred embodiment, the nucleic acid sequence is the mature polypeptide coding region of SEQ ID NO.1. In another preferred embodiment, the nucleic acid sequence is the mature polypeptide coding region contained in plasmid pTri5 that is contained in *Escherichia coli* NRRL B-30029. The present invention also encompasses nucleic acid sequences which encode a polypeptide having the amino acid sequence of SEQ ID NO. 2, which differ from SEQ ID NO. 1 by virtue of the degeneracy of the genetic code. The present invention also relates to subsequences of SEQ ID NO.1 which encode fragments of SEQ ID NO. 2 that have trichodiene synthase activity.

A subsequence of SEQ ID NO.1 is a nucleic acid sequence encompassed by SEQ ID NO. 1 except that one or more nucleotides from the 5' and/or 3' end have been deleted. Preferably, a subsequence contains at least 870 nucleotides, more preferably at least 960 nucleotides, and most preferably at least 1050 nucleotides.

The present invention also relates to mutant nucleic acid sequences comprising at least one mutation in the mature polypeptide coding sequence of SEQ ID NO. 1, in which the mutant nucleic acid sequence encodes a polypeptide which consists of amino acids 1 to 380 of SEQ ID NO. 2.

The techniques used to isolate or clone a nucleic acid sequence encoding a polypeptide are described herein. The nucleic acid sequence may be cloned from a strain of *Fusarium*, or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The present invention also relates to nucleic acid sequences which have a degree of homology to nucleotides 2521 to 3686 of SEQ ID NO. 1 of at least about 97% homology, which encode a trichodiene synthase. For purposes of the present invention, the degree of homology between two nucleic acid sequences is determined by the Wilbur-Lipman method (Wilbur and Lipman, 1983, *Proceedings of the National Academy of Science USA* 80: 726-730) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters are Ktuple=3, gap penalty=3, and windows=20.

Modification of a nucleic acid sequence encoding a trichodiene synthase of the present invention may be necessary for the synthesis of polypeptides substantially similar to the trichodiene synthase. The term "substantially similar" to the trichodiene synthase refers to non-naturally occurring forms of the polypeptide. These polypeptides may differ in some engineered way from the trichodiene synthase isolated from its native source, e.g., variants that differ in specific activity, thermostability, pH optimum, or the like. The variant sequence may be constructed on the basis of the nucleic acid sequence presented as the polypeptide encoding part of SEQ ID NO. 1, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for trichodiene synthase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

The present invention also relates to isolated nucleic acid sequences encoding a trichodiene synthase of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of SEQ ID NO. 1 or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) nucleotides 2521 to 3686 of SEQ ID NO. 1, (ii) the cDNA sequence contained in nucleotides 2521 to 3686 of SEQ ID NO. 1, (iii) a subsequence of (i) or (ii), or (iv) a complementary strand of (i), (ii), or (iii); and (b) isolating the nucleic acid sequence. The subsequence is preferably a sequence of at least 100 nucleotides such as a sequence which encodes a polypeptide fragment which has trichodiene synthase activity.

In a preferred embodiment, the isolated nucleic acid sequence encoding a trichodiene synthase is obtained from *Fusarium venenatum*, and in a more preferred embodiment, the nucleic acid sequence is obtained from *Fusarium venenatum* ATCC 20334, e.g., the nucleic acid sequence set forth in SEQ ID NO. 1. In another more preferred embodiment, the nucleic acid sequence is the sequence contained in plasmid pTri5 which is contained in *Escherichia coli* NRRL B-30029. The present invention also encompasses nucleic acid sequences which differ from SEQ ID NO. 1 by virtue of the degeneracy of the genetic code.

The nucleic acid sequences may be obtained from microorganisms which are taxonomic equivalents of *Fusarium venenatum* as defined by Yoder and Christianson, 1998, supra, and O'Donnell et al., 1998, supra, regardless of the species name by which they are currently known.

The present invention further relates to methods for producing a mutant nucleic acid sequence, comprising introducing at least one mutation into the mature polypeptide coding sequence of SEQ ID NO. 1 or a subsequence thereof, wherein the mutant nucleic acid sequence encodes a polypeptide which consists of amino acids 1 to 380 of SEQ ID NO. 2 or a fragment thereof which has trichodiene synthase activity.

The introduction of a mutation into the nucleic acid sequence to exchange one nucleotide for another nucleotide may be accomplished by site-directed mutagenesis using any of the methods known in the art. Particularly useful is the procedure which utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used.

The present invention also relates to nucleic acid constructs, recombinant expression vectors, and host cells containing the nucleic acid sequence of SEQ ID NO. 1, subsequences or homologues thereof, for expression of the sequences. The constructs and vectors may be constructed as described herein. The host cell may be any cell suitable for the expression of the nucleic acid sequence. The term "host cell" encompasses any progeny of a parent cell that is not identical to the parent cell due to mutations that occur during replication. The choice of a host cell will to a large extent depend upon the gene encoding the polypeptide and its source.

The host cell may be a eukaryote, such as a mammalian, insect, plant, or fungal cell.

In a preferred embodiment, the host cell is a fungal cell. "Fungi" as used herein includes the phyla Ascomycota, Basidiomycota, Chytridiomycota, and Zygomycota (as defined by Hawksworth et al., *In, Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No*. 9, 1980).

In an even more preferred embodiment, the yeast host cell is a *Candida, Hansenula, Kluyveromyces, Pichia, Saccharomyces, Schizosaccharomyces*, or *Yarrowia* cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another most preferred embodiment, the yeast host cell is a *Yarrowia lipolytica* cell.

In another more preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred embodiment, the filamentous fungal host cell is a cell of a species of, but not limited to, *Acremonium, Aspergillus, Fusarium, Humicola, Mucor, Myceliophthora, Neurospora, Penicillium, Thielavia, Tolypocladium*, or *Trichoderma*.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides*, or *Fusarium venenatum* cell. In an even most preferred embodiment, the filamentous fungal parent cell is a *Fusarium venenatum* (Nirenberg sp. nov.) cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei*, or *Trichoderma viride* cell.

Filamentous fungal cells may be transformed using the procedures described herein. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

The present invention also relates to methods for producing a trichodiene synthase of the present invention comprising (a) cultivating a strain, which in its wild-type form is capable of producing the polypeptide, to produce a supernatant comprising the trichodiene synthase; and (b) recovering the trichodiene synthase. Preferably, the strain is of the genus *Fusarium*, and more preferably *Fusarium venenatum.*

The present invention also relates to methods for producing a trichodiene synthase of the present invention comprising (a) cultivating a host cell under conditions conducive for production of the trichodiene synthase; and (b) recovering the trichodiene synthase.

The present invention further relates to methods for producing a trichodiene synthase comprising (a) cultivating a homologously recombinant cell, having incorporated therein a new transcription unit comprising a regulatory sequence, an exon, and/or a splice donor site operably linked to a second exon of a nucleic acid sequence of the present invention which is endogenous to a cell, under conditions suitable for production of the trichodiene synthase encoded by the endogenous nucleic acid sequence; and (b) recovering the trichodiene synthase. The methods are based on the use of gene activation technology, for example, as described in U.S. Pat. No. 5,641,670.

In the production methods of the present invention, the cells are cultivated in a nutrient medium suitable for production of the trichodiene synthase using methods known in the art as described herein. The trichodiene synthase may be detected using methods known in the art specific for the enzyme (see, e.g., Hohn and Beremand, 1989, *Applied and Environmental Microbiology* 55: 1500-1503). The resulting trichodiene synthase may be recovered and purified by methods known in the art as described herein.

Nitrate Reductase Selectable Marker-Free Mutant Cells

The present invention also discloses the use of a nitrate reductase gene as a selectable marker for modifying a target gene or DNA element to reduce or eliminate the production of a gene product in a cell. The nitrate reductase gene may then be deleted from the cell to produce a cell that is free of the selectable marker.

The present invention therefore also relates to methods for obtaining a mutant cell, comprising: (a) introducing into a parent cell, having a nucleic acid sequence encoding a gene product, a nucleic acid construct comprising a nitrate reductase gene as a selectable marker and a modification of the nucleic acid sequence, wherein the construct incorporates into the genome of the parent cell replacing the nucleic acid sequence resulting in reduced production of the gene product compared to the parent cell when cultivated under the same conditions; and (b) selecting a mutant cell from step (a) for the presence of the nitrate reductase gene and reduced production of the gene product.

Nitrate reductase catalyzes the conversion of nitrate to nitrite which allows a cell to grow on nitrate as the sole nitrogen source. For cells that lack the possibility or only have a very limited capacity to use nitrate as the sole nitrogen source, the nitrate reductase gene in principle can be used as a selectable marker provided that nitrate is taken up by the cell. The nitrate reductase gene is preferably dominant in the cell of choice. The DNA coding for the nitrate reductase may be of genomic, cDNA, RNA, semi-synthetic, synthetic origin, or any combinations thereof, which produce a functional form of the enzyme.

The nitrate reductase gene may be obtained from any source using any of the recombinant methods described herein or known in the art. In a preferred embodiment, the nitrate reductase gene is obtained from a fungal source, and more preferably from a yeast or filamentous fungal strain. In a more preferred embodiment, the nitrate reductase gene is obtained from *Neurospora crassa* (nit3, see, Fu and Marzluf, 1987, *Proceedings of the National Academy of Sciences USA* 84: 8243-8247). In another more preferred embodiment, the nitrate reductase gene is obtained from an *Aspergillus strain* (niaD), such as *Aspergillus nidulans, Aspergillus niger, Aspergillus oryzae*, and *Aspergillus parasiticus*. In another more preferred embodiment, the nitrate reductase gene is obtained from a *Fusarium* strain (nia), such as *Fusarium oxysporum.*

Modification of a target nucleic acid sequence may be accomplished using the methods for gene insertions, disruptions, replacements, or deletions described herein or known in the art. The genetic modification may be one or more nucleotide alterations, e.g., insertions, deletions, and/or substitutions of the target nucleic acid sequence or a portion thereof such as, but not limited to, a coding region, signal sequence, promoter, terminator, intron, or regulatory DNA sequence. A nucleic acid construct comprising a modified version of the target nucleic acid sequence, or a portion thereof, is therefore constructed for the purpose of eliminating or reducing expression of the nucleic acid sequence. The construct is then transformed into the parent cell to produce a defective nucleic acid sequence where, by homologous recombination, the defective sequence replaces the target sequence or a portion thereof. The construct may be contained on a vector for introduction into the cell. The nitrate reductase gene is used as a selectable marker for identifying transformants containing the defective nucleic acid sequence.

The defective nucleic acid sequence may be a simple disruption of the target sequence with a nitrate reductase gene. Alternatively, the defective nucleic acid sequence may contain an insertion, substitution, and/or deletion of the target sequence, or a portion thereof, in addition to a disruption carried by the nitrate reductase gene. Furthermore, the defective nucleic acid sequence may contain an insertion, substitution, and/or deletion of the target sequence, or a portion thereof, where the nitrate reductase gene is not involved in the modification, but where the latter is contiguous with the defective sequence.

The nucleic acid construct may further comprise one or more repeat sequences at the 5' and 3' ends of the nitrate reductase gene to facilitate eventual deletion of the nitrate reductase gene. The repeats may be any nucleic acid sequence suitable for facilitating intrachromosomal homologous recombination. The frequency of marker deletion is substantially increased by increasing the capacity of the gene to undergo intrachromosomal homologous recombination.

A useful property of the nitrate reductase is that it is able to convert chlorate to chlorite, which is toxic to cells. It is this property that forms the basis for another aspect of the present invention, i.e., the production of transformants free of the nitrate reductase selectable marker. The chlorate converting property enables the counter-selection of transformed cells. Selected transformants containing the nitrate reductase gene are grown on a medium containing chlorate as the sole nitrogen source to identify those surviving transformants which have lost the nitrate reductase gene. Some of the surviving transformants may have mutations in the nitrate reductase gene itself. Therefore, deletion of the nitrate reductase gene should be confirmed, e.g., by Southern hybridization.

Therefore, the methods for obtaining a mutant cell may further comprise (c) selecting a mutant cell from step (b) under culturing conditions in which the nitrate reductase gene is deleted. Alternatively, the methods for obtaining a mutant cell may further comprise (c) introducing into the mutant cell from step (b) a second nucleic acid construct comprising a second nucleic acid sequence comprising 5' and 3' regions of the modified nucleic acid sequence, but lacking the nitrate reductase gene, wherein the second construct incorporates into the genome of the parent cell replacing the modified nucleic acid sequence with the second nucleic acid sequence; and (d) selecting a mutant cell from step (c) under culturing conditions in which the nitrate reductase gene is deleted.

In both cases, the culturing conditions involve a counter-selection medium for nitrate reductase comprising chlorate.

A preferred construct for deleting a nitrate reductase gene as a selectable marker would contain the following elements in a 5' to 3' order: sequences 5' of the gene to be deleted, directly fused to sequences 3' of the gene to be deleted, followed downstream by a functional nitrate reductase gene, followed downstream by again sequences 3' of the gene to be deleted. In this case, both sequences 3' of the gene to be deleted are chosen such that they form repeats flanking the selectable marker gene. Transformation of this nucleic acid construct and subsequent replacement of the chromosome copy of the gene to be deleted by the nucleic acid construct with cross-over points in the sequences 5' and 3' of the gene to be deleted results in deletion of the gene. Subsequent intrachromosomal recombination between the repeats flanking the selectable marker gene and counter-selection for these transformants finally results in a selection marker-free strain. The 5' and 3' repeats do not necessarily need to both be present in the construct, since single repeats may be used to delete the gene by a single cross-over integration. The construct(s) may be constructed in such a way that after deletion of the nitrate reductase gene, no extraneous nitrate reductase gene DNA remains in the chromosome of the transformed cell.

The construct(s) may be contained in a vector. The constructs and vectors may be prepared as described herein.

The methods of the present invention may be used to reduce or eliminate the production of one or more target gene products which are undesirable in the production of a protein (or compound) of interest, particularly where the target gene product(s) may be detrimental to the production, recovery, and/or application of the protein or compound. The methods may also be used to reduce or eliminate the biosynthesis of antibiotics and other bioactive compounds.

The cell may be a unicellular microorganism, e.g., a prokaryote, or a non-unicellular microorganism, e.g., a eukaryote such as a mammalian, insect, plant, or fungal cell.

In a preferred embodiment, the host cell is a fungal cell, such as a yeast or filamentous fungal cell. The yeast or fungal cell may be any of the cells described herein.

Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis*, and *Bacillus thuringiensis*; or a *Streptomyces* cell, e.g., *Streptomyces lividans* or *Streptomyces murinus*, or gram negative bacteria such as *E. coli* and *Pseudomonas* sp.

The introduction of the construct into a bacterial cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The present invention also relates to mutant cells produced by such methods. The mutant cells of the present invention may be used for the production of a polypeptide native or foreign to the mutant cell. The polypeptide may be any polypeptide such as those described herein. Expression of a polypeptide in a mutant cell of the present invention may be accomplished using the methods described herein.

The present invention also relates to methods for producing a polypeptide, comprising: (a) cultivating such a mutant cell comprising a nucleic acid sequence encoding a polypeptide under conditions conducive for the production of the polypeptide; and (b) isolating the polypeptide from the cultivation medium of the mutant cell. Methods for cultivation of a mutant and isolation of the polypeptide are described herein.

The present invention is further described by the following examples which should not be construed as limiting the scope of the invention.

EXAMPLES

Materials

Chemicals used as buffers and substrates were commercial products of at least reagent grade.

Strains

*Fusarium* strain A3/5, now reclassified as *Fusarium venenatum* (Yoder and Christianson, 1998, *Fungal Genetics and Biology* 23: 62-80; O'Donnell et al., 1998, *Fungal Genetics and Biology* 23: 57-67), was obtained from Dr. Anthony Trinci, Universisty of Manchester, Manchester, England, or from the American Type Culture Collection, Manassas, Va., as *Fusarium* strain ATCC 20334. *Fusarium venenatum* strain #93 (BBA 64537) was obtained from Biologische Bundensanstalt fur Land- und Fortswirtschaft, Berlin, Germany. Morphological mutants of *Fusarium venenatum* A3/5 designated CC1-1, CC1-2, CC1-3, CC1-5, CC1-8, CC2-3, MC3-2, MC3-5, MC3-6, and MC3-9 (Wiebe et al., 1992, *Mycological Research* 96: 555-562; Wiebe et al., 1991, *Mycological Research* 95: 1284-1288; Wiebe et al., 1991, *Mycological Research* 96: 555-562) are highly branched, colonial variants. All of the following strains were derived from the *Fusarium venenatum* A3/5 morphological mutant CC1-3: *Fusarium venenatum* MLY3 (a derivative of CC1-3 which has identical complementation characteristics to CC1-3); *Fusarium venenatum* JRoy36-19B (CC1-3, xylanase$^+$, bar$^+$); *Fusarium venenatum* LyMC4 (CC1-3, tri5-deleted, amdS$^+$, bar$^+$, xylanase$^+$); *Fusarium venenatum* LyMC4. B (CC1-3, tri5-deleted, amdS$^+$, bar$^+$, xylanase$^+$, single-spore isolate of LyMC4); *Fusarium venenatum* LyMC4. C (CC1-3, tri5-deleted, amdS$^+$, bar$^+$, xylanase$^+$, single-spore isolate of LyMC4); *Fusarium venenatum* LyMC19 (CC1-3,tri5-deleted, amdS$^+$, bar$^+$, xylanase$^+$); *Fusarium venenatum* LyMC19.2 (CC1-3, tri5-deleted, amdS$^+$, bar$^+$, xylanase$^+$, single-spore isolate of LyMC19); *Fusarium venenatum* LyMC19.5 (CC1-3, tri5-deleted, amdS$^+$, bar$^+$, xylanase+, single-spore isolate of LyMC19); *Fusarium venenatum* LyMC1 (MLY3, tri5-deleted); *Fusarium venenatum* LyMC1A (MLY3, tri5-deleted, amdS, single-spore isolate); *Fusarium venenatum* LyMC1B (MLY3, tri5-deleted, amdS, single-spore isolate); and *Fusarium venenatum* LyMC1C (MLY3, tri5-deleted, amdS, single-spore isolate).

Media and Solutions

AMG trace metals solution was composed per liter of 14.3 g of $ZnSO_4.7H_2O$, 2.5 g of $CuSO_4.5H_2O$, 0.5 g of $NiCl_2$, 13.8 g of $FeSO_4$, 8.5 g of $MnSO_4$, and 3.0 g of citric acid.

Biotin stock solution was composed of 5 mg of biotin in 100 ml of 50% ethanol.

COVE trace metals solution was composed per liter of 0.04 g of $NaB_4.O_7.10H_2O$, 0.4 g of $CuSO_4.5H_2O$, 1.2 g of $FeSO_4.7H_2O$, 0.7 g of $MnSO_4.H_2O$, 0.8 g of $Na_2MoO_2.2H_2O$, and 10 g of $ZnSO_4.7H_2O$.

50× COVE salts solution was composed per liter of 26 g of KCl, 26 g of $MgSO_4.7H_2O$, 76 g of $KH_2PO_4$, and 50 ml of COVE trace metals.

COVE medium was composed per liter of 342.3 g of sucrose, 20 ml of 50× COVE salt solution, 1 mM acetamide, 1.5 mM $CsCl_2$, and 25 g of Noble agar.

50× Vogels medium was composed per liter of 150 g of sodium citrate, 250 g of $KH_2.PO_4$, 10 g of $MgSO_4.7H_2O$, 10 g of $CaCl_2.2H_2O$, 2.5 ml of biotin stock solution, and 5.0 ml of AMG trace metals solution.

COVE top agarose was composed per liter of 20 ml of 50× COVE salts, 0.8 M sucrose, 15 mM cesium chloride, 10 mM acetamide, and 10 g of low melt agarose, pH adjusted to 6.0.

NY50 medium was composed per liter of 62.5 g of Nutriose 725, 2 g of $MgSO_4.7H_2O$, 10 g of $KH_2PO_4$, 2 g of $K_2SO_4$, 2 g of citric acid, 10 g of yeast extract, 2 g of urea, 0.5 g of $CaCl_2.2H_2O$, and 0.5 ml of AMG trace metals, pH 6.0.

NYU35 medium was composed per liter of 35 g of maltodextrin, 1 g of $MgSO_4.7H_2O$, 2 g of $KH_2PO_4$, 2 g of citric acid, 4 g of yeast extract, 1 g of urea, and 0.25 ml of AMG trace metals, pH 6.0.

RA sporulation medium was composed per liter of 50 g of succinic acid, 12.1 g of $NaNO_3$, 1 g of glucose, 20 ml of 50× Vogels, and 0.5 ml of a 10 mg/ml $NaMoO_4$ stock solution, pH to 6.0.

YEG medium was composed per liter of 5 g of yeast extract and 20 g of glucose.

YEP medium was composed per liter of 10 g of yeast extract and 20 g of peptone.

YEPG medium was composed per liter of 10 g of yeast extract, 20 g of peptone, and 20 g of glucose.

Minimal medium was composed per liter of 6 g of $NaNO_3$, 0.52 g of KCl, 1.52 g of $KH_2PO_4$, 1 ml of COVE trace metals solution, 1 g of glucose, 500 mg of $MgSO_4.7H_2O$, 342.3 g of sucrose, and 20 g of Noble agar at pH 6.5).

STC was composed of 0.8 M sorbitol, 25 mM Tris pH 8, 25 mM $CaCl_2$.

SPTC was composed of 40% PEG 4000, 0.8 M sorbitol, 25 mM Tris pH 8, 25 mM $CaCl_2$.

M400Da medium was composed per liter of 50 g of maltodextrin, 2 g of $MgSO_4.7H_2O$, 2 g of $KH_2PO_4$, 4 g of citric acid, 8 g of yeast extract, 2 g of urea, and 1 ml of COVE trace metals solution.

Sporulation III medium was composed per liter of 20 mls of 50× Vogels, 4 g of glucose, 0.8 g of $NaNO_3$, and 1 ml of a 10 mg/ml $NaMoO_4$ stock solution.

Vogels medium with BASTA™ (first stage seed inoculation) was composed of 20 ml of 50× Vogels, 5% glucose, 16.5 g of monobasic ammonium phosphate per liter, and 5 mg of BASTA™ per ml, pH 6.5.

Potassium chlorate medium for selection of niaD mutants was composed per liter of 20 mls of 50× COVE salts solution, 61.28 g of potassium chlorate, 0.3 g of urea, 25 g of noble agar, and 2% glucose added after autoclaving.

Fluoroacetamide medium was composed per liter of 12 g of sodium acetate, 2 g of sodium chloride, 0.5 g of $MgSO_4$, 3 g of $KH_2PO_4$, 0.3 g of urea, 2 g of fluoroacetamide, 1 ml of Vogels salts, and 15 g of Noble agar, pH 6.1.

TAE buffer was composed per liter of 4.84 g of Tris Base, 1.14 ml of glacial acetic acid, and 2 ml of 0.5 M EDTA pH 8.0.

Example 1

*Fusarium venenatum* ATCC 20334 Genomic DNA Extraction

*Fusarium venenatum* ATCC 20334 was grown in 25 ml of YEG medium for 24 hours at 28° C. and 150 rpm. Mycelia were then collected by filtration through Miracloth (Calbiochem, La Jolla, Calif.) and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to ensure mixing, and extracted twice with an equal volume of phenol: chloroform:isoamyl alcohol (25:24:1 v/v/v). Sodium acetate (3 M solution) was added to give a final concentration of 0.3 M and the nucleic acids were precipitated with 2.5 volumes of ice cold ethanol. The tube was centrifuged at 15,000×g for 30 minutes and the pellet was allowed to air dry for 30 minutes before resuspension in 0.5 ml of TE buffer.

DNase-free ribonuclease A was added to a concentration of 100 mg/ml and the mixture was incubated at 37° C. for 30 min. Proteinase K (200 mg/ml) was then added and the mixture was incubated an additional hour at 37° C. Finally, the mixture was extracted twice with phenol:chloroform: isoamyl alcohol (25:24:1 v/v/v) before precipitating the DNA with sodium acetate and ethanol according to standard procedures. The DNA pellet was dried under vacuum, resuspended in TE buffer, and stored at 4° C.

Example 2

Preparation of a *Fusarium venenatum* ATCC 20334 Trichodiene Synthase Probe

Based on the conserved amino acid sequences of the trichodiene synthases from *Fusarium sporotrichioides*, *Fusarium poae*, and *Gibberella pulicaris*, the oligonucleotide primers shown below were synthesized with an Applied Biosystems Model 394 DNA/RNA Synthesizer, according to the manufacturer's instructions, to PCR amplify a trichodiene synthase gene fragment from *Fusarium venenatum* ATCC 20334 genomic DNA.

```
Primer 1: 5'-GGCTGCTCATCACTTTGCTC-3' (SEQ ID NO. 3)

Primer 2: 5'-TGCATGAAGCACTCAATCGT-3' (SEQ ID NO. 4)
```

Amplification reactions (50 μl) were prepared using approximately 0.8 μg of *Fusarium venenatum* genomic DNA, prepared as described in Example 1, as the template. Each reaction contained the following components: 0.8 μg of genomic DNA, 40 pmol of primer 1, 40 pmol of primer 2, 200 μM each of dATP, dCTP, dGTP, and dTTP, 1× Taq DNA polymerase buffer (Perkin-Elmer Corp., Branchburg, N.J.), and 2.5 Units of Taq DNA polymerase (Perkin-Elmer Corp., Branchburg, N.J.). The reactions were incubated in a Perkin-Elmer Model 480 Thermal Cycler programmed for 30 cycles each at 95° C. for 3 minutes, 58° C. for 2 minutes, and 72° C. for 2 minutes. The reaction products were isolated on a 1.5% agarose gel (Eastman Kodak, Rochester, N.Y.) where a 812 bp product band was excised from the gel and purified using Qiaex II (Qiagen, Chatsworth, Calif.) according to the manufacturer's instructions. The purified PCR product was subsequently cloned into a pCRII vector (Invitrogen, San Diego, Calif.) and the DNA sequence was determined using lac forward and reverse primers (New England BioLabs, Beverly, Mass.).

DNA sequence analysis showed that the amplified gene fragment encoded a portion of the corresponding *Fusarium venenatum* trichodiene synthase gene based on sequence comparison with the *Fusarium sporotrichioides, Fusarium poae*, and *Gibberella pulicaris* trichodiene synthase gene sequences. The trichodiene synthase gene fragment (812 kb) was PCR-labeled with digoxygenin using a DIG Kit (Boehringer Mannheim Corp., Indianapolis, Ind.) according to the manufacturer's instructions to probe a *Fusarium venenatum* genomic DNA library.

Example 3

DNA Libraries and Identification of tri5 Clones

Genomic DNA libraries were constructed using the bacteriophage cloning vector λZipLox (Life Technologies, Gaithersburg, Md.) with *E. coli* Y1090ZL cells (Life Technologies, Gaithersburg, Md.) as a host for plating and purification of recombinant bacteriophage and *E. coli* DH10Bzip (Life Technologies, Gaithersburg, Md.) for excision of individual pZL1-tri5 clones. Total cellular DNA was partially digested with Tsp509I and size-fractionated on 1% agarose gels. DNA fragments migrating in the size range 3-8 kb were excised and eluted from the gel using Qiaex (Qiagen Inc., Chatsworth Calif.). The eluted DNA fragments were ligated with EcoRI-cleaved and dephosphorylated λZipLox vector arms (Life Technologies, Gaithersburg, Md.), and the ligation mixtures were packaged using commercial packaging extracts (Stratagene, La Jolla, Calif.). The packaged DNA libraries were plated and amplified in *Escherichia coli* Y1090ZL cells (Life Technologies, Gaithersburg, Md.). The amplified genomic library contained $1.4\times10^7$ pfu/ml. Approximately 30,000 plaques from the library were screened by plaque-hybridization with the non-radioactive digoxygenin described in Example 2 using standard procedures (see, Sambrook et al., 1989, supra).

Three positive clones which hybridized strongly to the probe were picked and two were purified twice in *E. coli* Y1090ZL cells. The two tri5 clones, pSMO129 and pSMO130, were subsequently excised from the λZipLox vector as pZL1-tri5 clones (D'Alessio et al., 1992, Focus® 14: 76).

Example 4

DNA Sequence Analysis of *Fusarium venenatum* tri5 Gene

DNA sequencing of the tri5 clones, pSMO129 and pSMO130, was performed with an Applied Biosystems Model 373A Automated DNA Sequencer (Applied Biosystems, Inc., Foster City, Calif.). In addition to the lac-forward and lac-reverse primers, specific oligonucleotide sequencing primers were synthesized on an Applied Biosystems Model 394 DNA/RNA Synthesizer according to the manufacturer's instructions.

DNA sequencing of the clones designated pSMO129 and pSMO130 showed that neither clone contained the complete sequence of the gene, but contained overlapping sequences from which was obtained the DNA sequence of the entire gene. The combined DNA sequence of the two sequences revealed an open reading frame as shown in FIG. 2 (SEQ ID NO. 1).

A single clone containing the entire gene fragment was constructed from the two overlapping clones pSO130 and pSO129. pSO129 and pSO130 were digested with the restriction enzyme SacI and then run on a 1% agarose gel. The appropriate fragments were then gel isolated using a QIAquick Gel Extraction Kit (Qiagen, Chatsworth, Calif.) and ligated overnight at 14° C. using standard methods to produce pTri5. The ligation was then transformed into *E. coli* strain DH5α by standard methods. Plasmid DNA from a putative full length clone was isolated using a Qiagen MaxiPrep kit (Qiagen, Chatsworth, Calif.) and DNA sequenced using an Applied Biosystems Model 373A Automated DNA Sequencer which confirmed the sequence was identical to SEQ ID NO. 1. The clone was designated *E. coli* DH5α pTri5.

The positions of introns and exons within the *Fusarium venenatum* ATCC 20334 trichodiene synthase gene were assigned based on alignments of the deduced amino acid sequence (SEQ ID NO. 2) to the corresponding *Fusarium poae* trichodiene synthase gene product (SEQ ID NO. 5). On the basis of this comparison, the *Fusarium venenatum* ATCC 20334 trichodiene synthase gene was composed of 2 exons (1-469 bp and 529-1203 bp) which were interrupted by 1 small intron (470-528 bp). The size and composition of the intron were consistent with those of other fungal genes (Gurr et al., 1987, In Kinghorn, J. R. (ed.), *Gene Structure in Eukaryotic Microbes*, pp. 93-139, IRL Press, Oxford) in that it contained consensus splice donor and acceptor sequences as well as the consensus lariat sequence (PuCTPuAC) near the 3' end of each intervening sequence.

The trichodiene synthase is an acidic protein (calculated isoelectric point=5.37) composed of 380 amino acids (MW=44562).

A comparative alignment of trichodiene synthase deduced amino acid sequences was undertaken using the Clustal method (Higgins, 1989, *CABIOS* 5: 151-153) using the LASERGENE™ MEGALIGN™ software (DNASTAR, Inc., Madison, Wis.) with an identity table and the following multiple alignment parameters: Gap penalty of 10 and gap length penalty of 10. Pairwise alignment parameters were Ktuple=1, gap penalty=3, windows=5, and diagonals=5.

The comparative alignment showed that the deduced amino acid sequence of the *Fusarium venenatum* ATCC 20334 trichodiene synthase shared approximately 96.3% identity with the *Fusarium poae* trichodiene synthase (Fekete et al., 1997, *Mycopathologia* 138: 91-97) (SEQ ID NO. 5).

Example 5

Construction of pJRoy36 pJRoy36 was constructed to obtain expression of *Thermomyces lanuginosus* (formerly designated *Humicola lanuginosa*) xylanase in *Fusarium venenatum.* pDM181 was constructed using the technique of splice overlap extension to fuse the 1.2 kb *Fusarium oxysporum* trypsin promoter to the 1.1 kb *Fusarium oxysporum* trypsin terminator (SP387). A polylinker containing SwaI, KpnI and PacI restriction sites was inserted between the promoter and terminator as part of the overlapping PCR strategy. At the 5' end of the promoter a XhoI site was added and the native EcoRI site was preserved. At the 3' end of the terminator EcoRI, HindIII and NsiI sites were incorporated by the PCR reaction.

A PCR fragment containing −1208 to −1 of the *Fusarium oxysporum* trypsin promoter plus a 25 base pair polylinker was generated from plasmid pJRoy20 (Royer et al., 1995, *Biotechnology* 13: 1479-1483) using the following primers:

```
Primer I (sense):
      XhoI  EcoRI
5'-GAGCTCGAGGAATTCTTACAAACCTTCAAC-3'                 (SEQ ID NO. 6)

Primer 2 (antisense):
     PacI     KpnI        SwaI
5'-TTAATTAAGGTACCTGAATTTAAATGGTGAAGAGATAGATATCCAAG-3'  (SEQ ID NO. 7)
```

The 100 μl PCR reaction contained 1× Pwo buffer (Boehringer Mannheim, Indianapolis, Ind.), 200 μM each of dATP, dCTP, dGTP, and dTTP, 10 ng of pJRoy20, and 5 units of Pwo DNA polymerase (Boehringer Mannheim, Indianapolis, Ind.). PCR conditions used were 95° C. for 3 minutes followed by 25 cycles each at 95° C. for 30 seconds, 50° C. for 1 minute, and 72° C. for 1 minute. The final extension cycle was at 72° C. for 5 minutes.

Using the same PCR conditions, a second PCR fragment containing bp −5 to −1 of the *Fusarium oxysporum* trypsin promoter, a 25 base pair polylinker, and 1060 base pairs of the 3' untranslated region of the *Fusarium oxysporum* trypsin gene (terminator region) was generated from plasmid pJRoy20 using the following primers:

```
Primer 3 (sense):
          SwaI        KpnI      PacI
5'-TCACCATTTAAATTCAGGTACCTTAATTAAATTCCTTGTTGGAAGCGTCGA-3'  (SEQ ID NO. 8)

Primer 4 (antisense):
      NsiI HindIII EcoRI
5'-TGGTATGCATAAGCTTGAATTCAGGTAAACAAGATATAATTT-3'            (SEQ ID NO. 9)
```

The final 2.3 kb overlapping PCR fragment which contained −1208 to −1 of the *Fusarium oxysporum* trypsin promoter, the 25 base pair polylinker, and 1060 base pairs of the *Fusarium oxysporum* trypsin terminator was obtained using 0.2 μl of the first PCR (promoter) reaction and 3 μl of the second (terminator) reaction as templates and primers 1 and 4. The PCR conditions used were 95° C. for 3 minutes followed by 30 cycles each at 95° C. for 30 seconds, 62° C. for 1 minute, and 72° C. for 3 minutes. The final extension cycle was at 72° C. for 5 minutes. Pwo DNA polymerase was also used for this reaction.

Figure 3:
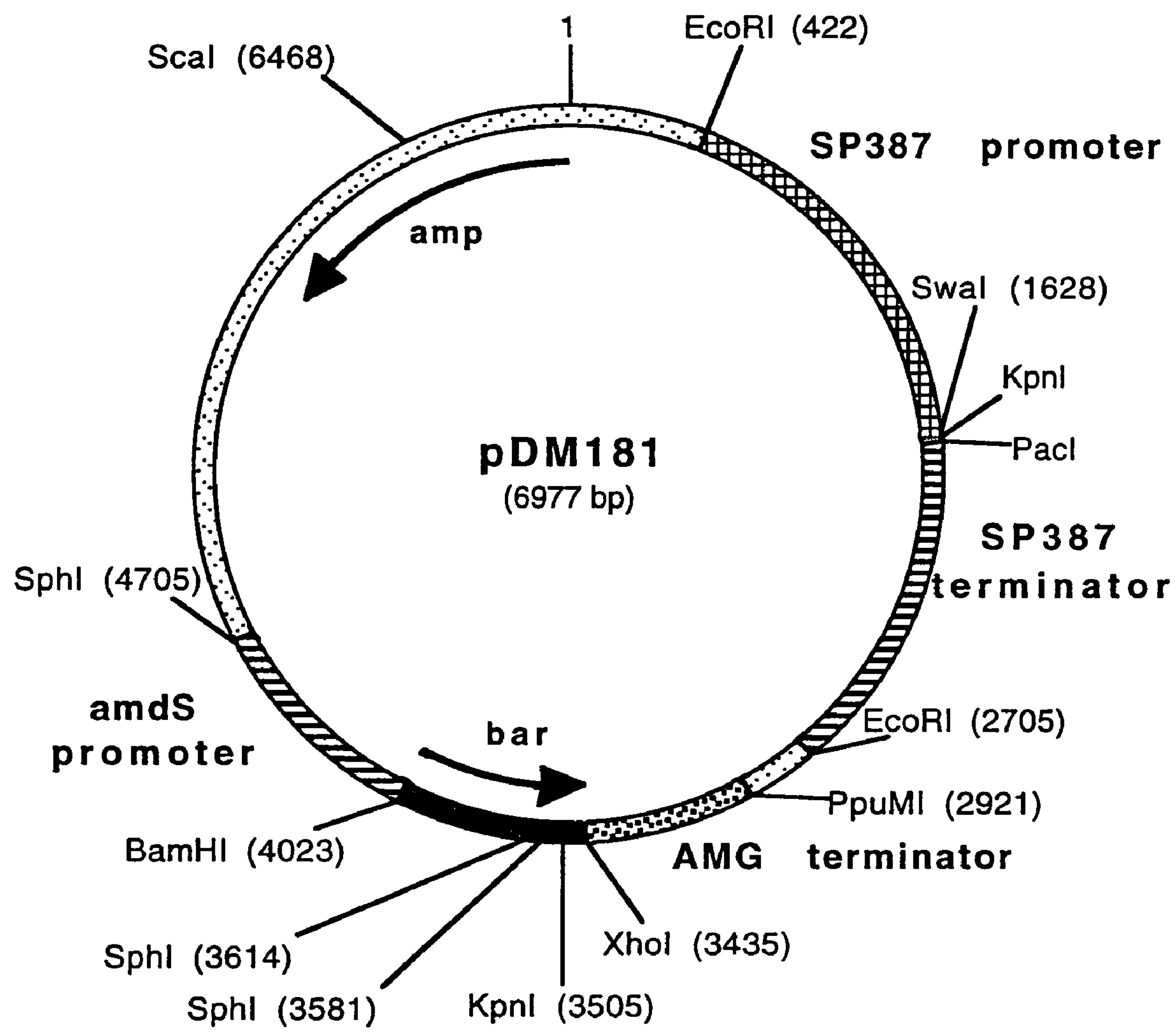
FIG. 3 shows a restriction map of pDM181.

The resulting 2.3 kb fragment containing the trypsin promoter, the polylinker, and the trypsin terminator was digested with EcoRI and ligated into the EcoRI digested vector pMT1612 containing the bar gene (WO 97/26330) to create pDM181 (FIG. 3).

The xylanase fragment was also generated by PCR. Plasmid pHD414 (WO 93/11249) which contains the cDNA of the *Thermomyces lanuginosus* xylanase gene was used as the template. PCR primers 5 and 6 were used to introduce the sequence CCACC at the 5' end and a PacI site at the 3' end of the xylanase coding sequence.

```
Primer 5 (sense)
5'-CCACCATGGTCGGCTTTACCCCCGTT-3'          (SEQ ID NO. 10)

Primer 6 (anti-sense)
5'-GGTTAATTAATTAGCCCACGTCAGCAACGGT-3'     (SEQ ID NO. 11)
        PacI
```

The PCR conditions used were 95° C. for three minutes followed by 25 cycles each at 95° C. for 1 minute, 62° C. for one minute, and 72° C. for three minutes. Reaction volumes were as previously described. DMSO was included at 5% v/v.

Figure 4:
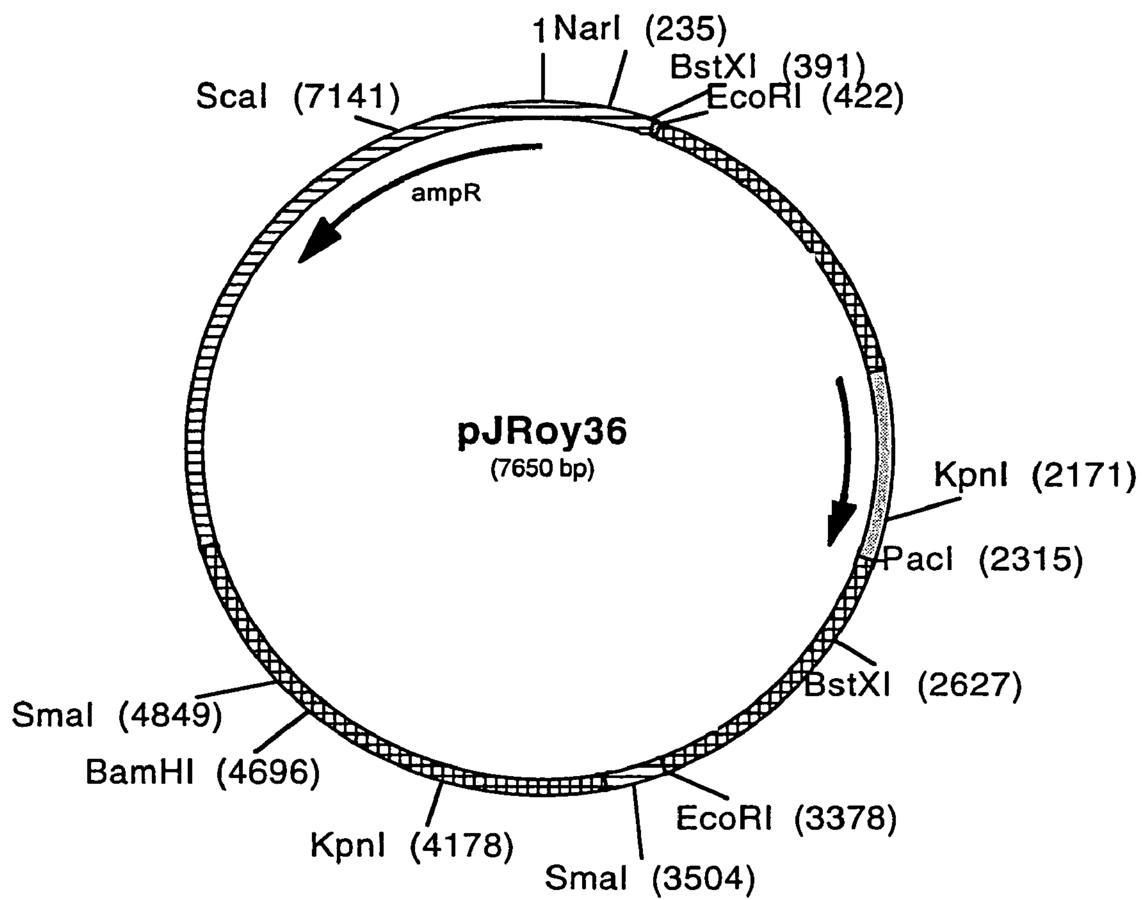
FIG. 4 shows a restriction map of pJRoy36.

The resulting 0.7 kb xylanase fragment was digested with PacI and ligated to SwaI/PacI digested pDM181 yielding plasmid pJRoy36 (FIG. 4).

Example 6

Construction of *Fusarium venenatum* JRoy36-19B and Expression of Xylanase Gene Spores of *Fusarium venenatum* CC1-3 were generated by inoculating a flask containing 500 ml of RA sporulation medium with 10 plugs from a 1× Vogels medium plate (2.5% Noble agar) supplemented with 2.5% glucose and 2.5 mM sodium nitrate and incubating at 28° C., 150 rpm for 2 to 3 days. Spores were harvested through Miracloth (Calbiochem, San Diego, Calif.) and centrifuged 20 minutes at 7000 rpm in a Sorvall RC-5B centrifuge (E. I. DuPont De Nemours and Co., Wilmington, Del.). Pelleted spores were washed twice with sterile distilled water, resuspended in a small volume of water, and then counted using a hemocytometer.

Protoplasts were prepared by inoculating 100 ml of YEPG medium with $4\times10^7$ spores of *Fusarium venenatum* CC1-3 and incubating for 16 hours at 24° C. and 150 rpm. The culture was centrifuged for 7 minutes at 3500 rpm in a Sorvall RT 6000D (E. I. DuPont De Nemours and Co., Wilmington, Del.). Pellets were washed twice with 30 ml of 1 M $MgSO_4$ and resuspended in 15 ml of 5 mg/ml of NOVOZYME 234™ (batch PPM 4356, Novo Nordisk A/S, Bagsvaerd, Denmark) in 1 M $MgSO_4$. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC:SPTC:DMSO to a final concentration of $1.25\times10^7$ protoplasts/ml. The protoplasts were stored at −80° C., after controlled-rate freezing in a Nalgene Cryo 1° C. Freezing Container (VWR Scientific, Inc., San Francisco, Calif.).

Frozen protoplasts of *Fusarium venenatum* CC1-3 were thawed on ice. Five μg of pJRoy36 described in Example 5 and 5 μl of heparin (5 mg per ml of STC) were added to a 50 ml sterile polypropylene tube. One hundred 1 μl of protoplasts were added, mixed gently, and incubated on ice for 30 minutes. One ml of SPTC was added and incubated 20 minutes at room temperature. After the addition of 25 ml of 40° C. COVE top agarose supplemented with 10-25 mM sodium nitrate in place of 10 mM acetamide and 10 mM cesium chloride, the mixture was poured onto an empty 150 mm diameter plate and incubated overnight at room temperature. Then an additional 25 ml of 40° C. COVE top agarose supplemented with 10-25 mM sodium nitrate in place of 10 mM acetamide and 10 mM cesium chloride and containing 10 mg of BASTA™ per ml was poured on top of the plate and incubated at room temperature for up to 14 days. The active ingredient in the herbicide BASTA™ is phosphinothricin. BASTA™ was obtained from AgrEvo (Hoechst Schering, Rodovre, Denmark) and was extracted twice with phenol:chloroform:isoamyl alcohol (25:24:1), and once with chloroform:isoamyl alcohol (24:1) before use.

Plugs from the plates (COVE underlay with COVE-BASTA™ overlay as above) of the transformants were inoculated into shake flasks containing 30 ml of M400Da medium and incubated at 30° C., 150 rpm for 7 days. Flasks were sampled at 7 days and supernatants were assayed for xylanase activity.

Xylanase activity was determined as follows. The reactions were initiated by the addition of 90 μl of a substrate solution containing 0.5% AZO-WAX™ (Megazyme, Dublin, Ireland) in 0.1 M sodium phosphate pH 6.0 buffer to 10 μl of each enzyme sample solution, diluted as appropriate in 0.1 M sodium phosphate pH 6.0 buffer. The reactions were incubated at 50° C. for 30 minutes and then quenched by adding 500 μl of ethanol that had been acidified with 0.55 μl of concentrated HCl. The resulting mixtures were allowed to stand at room temperature for at least 10 minutes, but no longer than 60 minutes. The samples were then centrifuged at 12,000 rpm for 2 minutes. A 200 μl aliquot of each supernatant was transferred to a microtiter plate and the absorbance was measured at 600 nm. Activity was calculated by reference to a BIOFEED WHEAT™ standard obtained from Novo Nordisk A/S, Bagsvaerd, Denmark, using a standard curve generated with a 1.0 FXU per ml standard added in volumes of 10, 20, 40, 60, 80, 90, and 100 μl. For this purpose, a 10 FXU/ml standard was prepared initially and then diluted 1:10 with 0.1 M sodium phosphate pH 6.0 buffer for use as the working standard. A blank (substitute buffer for enzyme) was included for generation of the standard curve using linear regression.

A single transformed colony designated *Fusarium venenatum* pJRoy36-19.B was selected based on the xylanase assay results.

Example 7

Construction of pJRoy40

Figure 5:
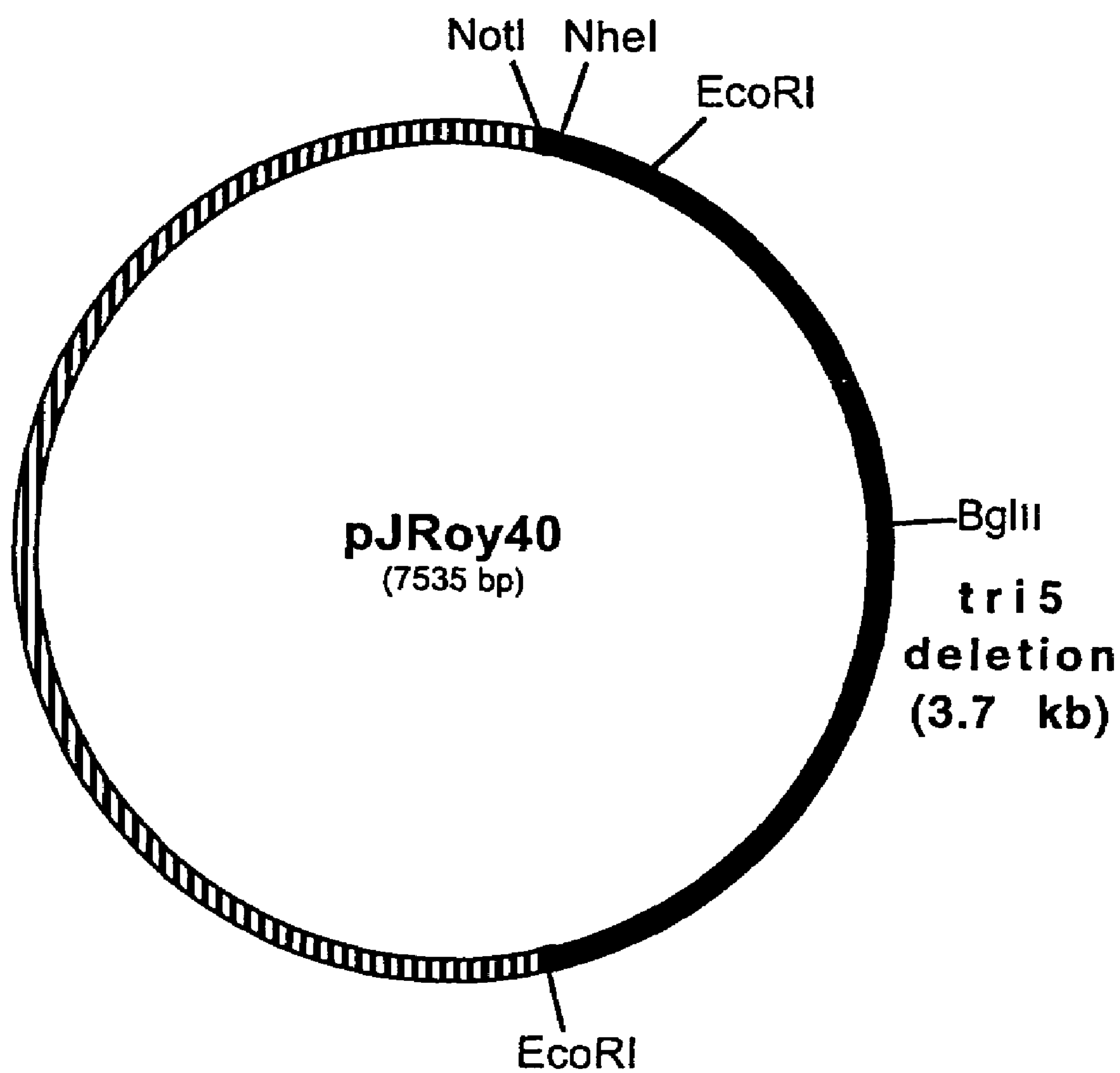
FIG. 5 shows a restriction map of pJRoy40.

A deletion plasmid, pJRoy40, was created which contained approximately 1.5 kb of 5' flanking DNA and 1.5 kb of 3' flanking DNA of the *Fusarium venenatum* tri5 gene joined by a BglII site. pSO129 and pSO130, described in Example 3, were digested with both NotI and BglII. The 5.5 kb fragment of pSO130, containing the vector pZL1 plus bp 0-1694 of tri5 DNA, was ligated to the 1.5 kb fragment of pSO129, corresponding to bp 5413-6946 of tri5 DNA plus a small amount of the polylinker. This resulted in pJRoy40 (FIG. 5) which contained 1.5 kb of tri5 5' DNA and 1.7 kb of tri5 3' DNA. The coding region for tri5 was bp 2475-3678. Approximately 3.7 kb of DNA, encompassing the entire tri5 coding region, had been removed.

Example 8

Figure 6:
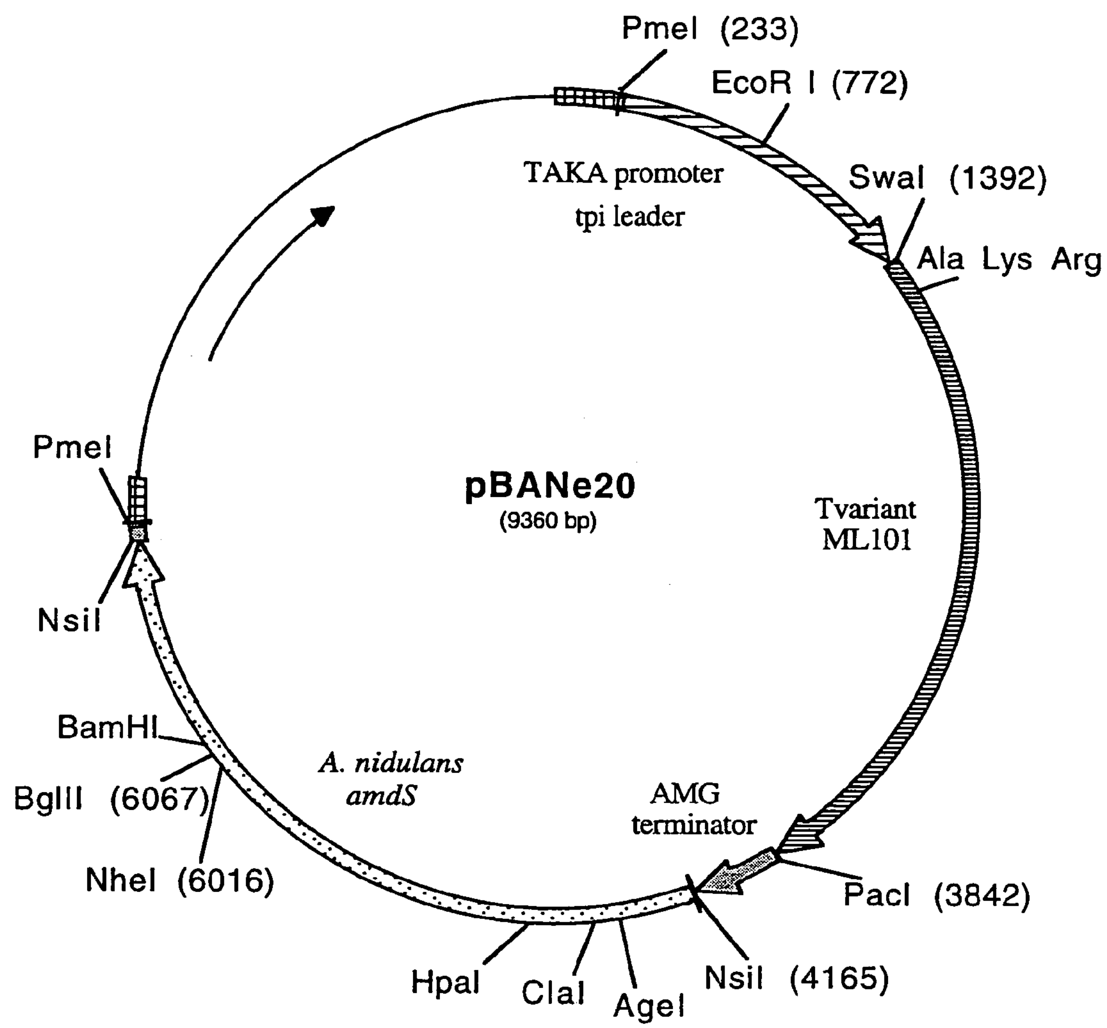
FIG. 6 shows a restriction map of pBANe20.
Figure 7:
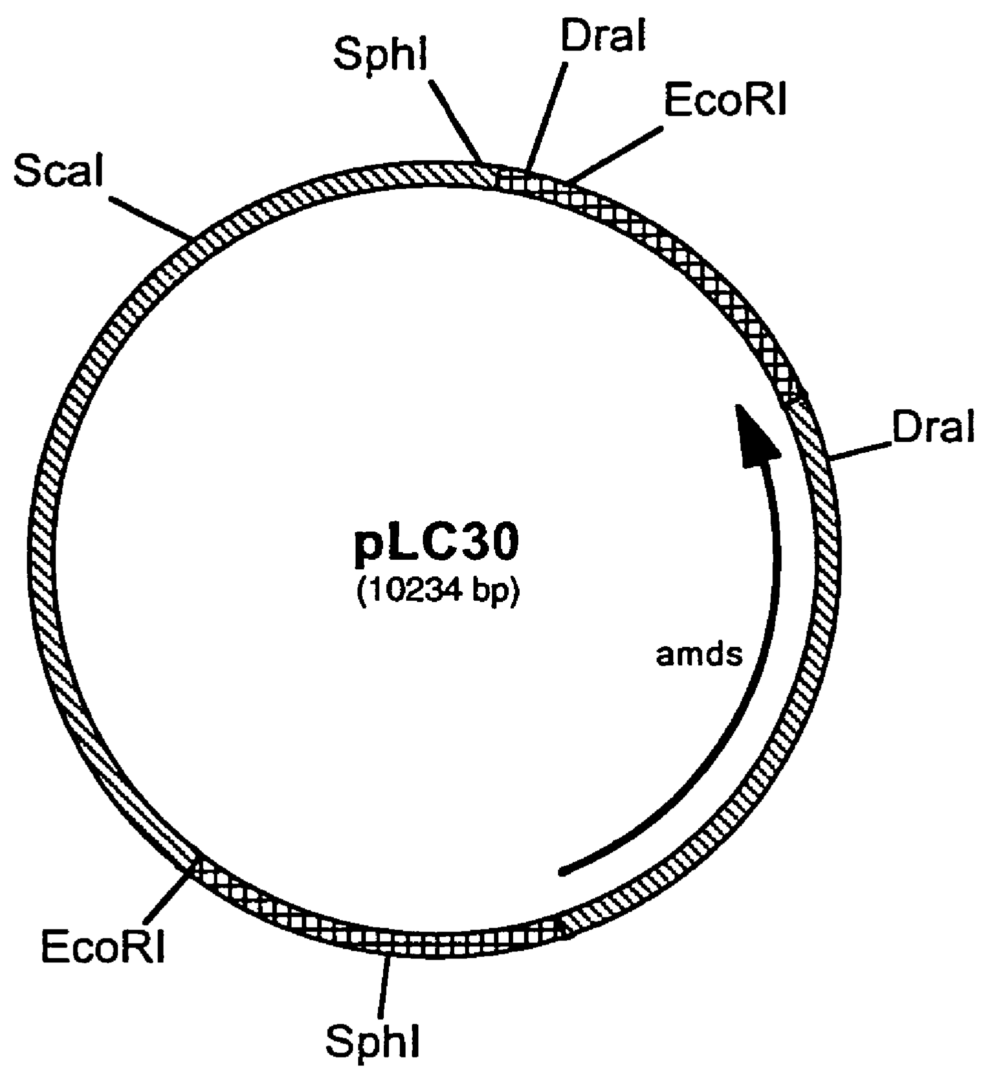
FIG. 7 shows a restriction map of pLC30.

Construction of tri5:: amdS Deletion Fragment pJRoy40 was digested with BglII, which forms the junction between the 5' and 3' regions. The ends were filled in with the Klenow fragment according to Sambrook et al., 1989, supra, and the linearized vector was purified by 1% agarose gel electrophoresis using TAE buffer and agarase treatment. The vector was next treated with calf intestinal alkaline phosphatase according to Sambrook et al., 1989, supra. The amdS gene was isolated from pBANe20 (FIG. 6) and inserted as a blunt fragment into the BglII site of pJRoy40, resulting in pLC30 (FIG. 7).

The 5670 bp EcoRI fragment containing the tri5 deletion cassette was isolated from pLC30 by gel purification using the QIAquick Gel Extraction Kit. The gel-purified deletion fragment was used to transform protoplasts of *Fusarium venenatum* JRoy36-19B.

Example 9

Construction of tri5 Hybridization Probes

DIG-labeled probes were obtained by PCR amplification. For a 5' probe ("tri5 flanking probe"), the amplification reaction contained the following components: 50 ng of pSO130, 100 μM each of DIG-labeled dATP, dCTP, dGTP, and dTTP, 50 pmoles each of primers tri5 5' probe 5'-AACTGGAAAGACCTGTGGGC-3' (bp 928-947) (SEQ ID NO. 12) and pSO130 5'-1442 probe 5'-GGGAAATAGTGTCACGCGGTA-3' (bp 1379-1399) (SEQ ID NO. 13), 2 units of Taq DNA polymerase, and 1× Taq DNA polymerase buffer. The reaction was incubated in a Perkin-Elmer Thermal Cycler programmed for 30 cycles each at 95° C. for 1 minute, 55° C. for 1 minute, and 72° C. for 90 seconds. The resulting fragment ("tri5 flanking probe") was gel isolated using GenElute Spin Columns (Supelco, Bellefonte, Calif.) and quantified with DIG Quantification Test Strips (Boehringer Mannheim, Indianapolis, Ind.) according to the manufacturers' instructions.

The conditions for generation of the open reading frame probe ("tri5 open reading frame probe") were identical, except that the following primers were used: primer 970590 5'-GGACAACAGCCGAACTCAAAC-3' (bp 2036-2057) (SEQ ID NO. 14) and primer 970478 5'-GTGCTGCGGATAAGGTTC-3' (bp 2919-2937) (SEQ ID NO. 15). The resulting fragment ("tri5 open reading frame probe") was isolated and quantified as above.

The fluorescein-labeled probes were made by amplifying the same PCR products as described above. The products were gel purified using the QIAquick Gel Extraction Kit according to the manufacturer's instructions. The purified fragments were fluorescein-labeled using the "Random Prime Labeling Module" for the Fluorimager (Amersham, Sunnyvale, Calif.) according to the manufactuer's instructions.

Example 10

Replacement of the *Fusarium venenatum* JRoy36-19B Native tri5 Gene with a Deletion Fragment Spores of *Fusarium venenatum* JRoy36-19B were generated by inoculating a flask containing 500 ml of RA sporulation medium with 10 plugs from an agar plate containing 5 mg of BASTA™ per ml and incubated at 28° C., 150 rpm for 2 to 3 days. Spores were harvested through Miracloth and centrifuged 20 minutes at 7000 rpm in a Sorvall RC-5B centrifuge. Pelleted spores were washed twice with sterile distilled water, resuspended in a small volume of water, and then counted using a hemocytometer.

Protoplasts were prepared by inoculating 100 ml of YEG medium with $4\times10^7$ spores of *Fusarium venenatum* JRoy36-19B and incubating for 16 hours at 24° C. and 150 rpm. The culture was centrifuged for 7 minutes at 3500 rpm in a Sorvall RT 6000D. Pellets were washed twice with 30 ml of 1 M $MgSO_4$ and resuspended in 20 ml of 5 mg/ml of NOVOZYME 234™ in 1 M $MgSO_4$. Cultures were incubated at 24° C. and 150 rpm until protoplasts formed. A volume of 35 ml of 2 M sorbitol was added to the protoplast digest and the mixture was centrifuged at 2500 rpm for 10 minutes. The pellet was resuspended, washed twice with STC, and centrifuged at 2000 rpm for 10 minutes to pellet the protoplasts. Protoplasts were counted with a hemocytometer and resuspended in an 8:2:0.1 solution of STC:

SPTC:DMSO to a final concentration of $1.25 \times 10^7$ protoplasts/ml. The protoplasts were stored at −80° C., after controlled-rate freezing in a Nalgene Cryo 1° C. Freezing Container.

Frozen protoplasts of *Fusarium venenatum* JRoy36-19B were thawed on ice. Five μg of the gel purified tri5 deletion fragment described in Example 8 were added to a 50 ml sterile polypropylene tube. One hundred μl of protoplasts were added, mixed gently, and incubated on ice for 30 minutes. One ml of SPTC was added and incubated 20 minutes at room temperature. After the addition of 25 ml of 40° C. COVE top agarose, the mixture was poured onto a 150 mM diameter COVE agar plate. Transformation plates were incubated at room temperature for up to 14 days.

Transformants were selected by growth on COVE plates, which required the ability to use acetamide as a nitrogen source and thus indicated the integration of the amdS gene. More than 145 transformants (from a total of 20 transformations) grew on the COVE plates, and 20 of these transformants were tested for 4,15-diacetoxyscirpenol (DAS) production.

DAS production was induced according to the following protocol. Spore stocks were generated by inoculation of 500 ml of RA sporulation medium in 2 liter Fernbach shake flasks with twelve agar plugs (~5×5 mm) cut from Minimal medium plates. The Fernbach shake flasks were incubated at 28° C. and 150 rpm for 40 hours. The cultures were then harvested through sterile Miracloth into sterile 50 ml Falcon tubes and their concentrations adjusted to $2 \times 10^7$ spores/ml, after counting using a haemocytometer slide. Spore stocks were either used immediately or stored at 5° C. for one or two weeks. Two ml of the $2 \times 10^7$ spores/ml spore stock (freshly generated or one or two weeks old) were inoculated into 50 ml of MYRO medium in 250 ml glass baffled shake flasks in triplicate. The shake flasks were incubated at 28° C. and 220 rpm, in the light, for 7 days. After 7 days, the contents of each shake flask were filtered through sterile Miracloth, their pH measured, and stored at −20° C. prior to DAS analysis.

DAS was extracted and quantified by the method of McCormick et. al., 1990, supra, with slight modifications. Cell-free *Fusarium venenatum* broth samples (1.0 ml) were extracted twice with two volumes of ethyl acetate (2.0 ml). The combined organic extracts were evaporated to dryness under a stream of nitrogen gas and derivatized with 50 microliters of TriSil/TBT (Pierce Chemical Co., Rockford, Ill.) at 80° C. for 60 minutes. The final sample volume was then adjusted to 0.5 ml with hexane.

One microliter of each sample was analyzed on a Hewlett-Packard 6890 gas chromatograph equipped with a 30 meter DB-1 column (J&W Scientific, Folsom, Calif.; 250 micrometer diameter, 0.25 micrometer film thickness) and FID detector. The injection procedure used the splitless mode with a 260° C. inlet and a nitrogen carrier gas flow of 1.2 ml/minute. The oven program was 180° C. initial temperature; heating at 30° C. per minute to 210° C.; heating at 5° C. per minute to 260° C.; and held at final temperature for 2 minutes.

Diacetoxyscirpenol identification and quantification was based on standard material obtained from Sigma Chemical Co. (St. Louis, Mo.). Under these conditions, the limit of detection was 2 ppm for DAS.

Twelve of the 20 transformants tested did not produce any detectable DAS. Plugs from the COVE plates of these twelve transformants were inoculated into triplicate shake flasks according to the following protocol for xylanase assays. A seed build-up method was used to inoculate shake flask cultures. Thirty ml of Vogels medium supplemented with 5 mg of BASTA™ per ml were inoculated with an agar plug from a fresh plate of each strain tested and then incubated 3 days at 28° C. at 200 rpm. One hundred and fifty μl of each culture were then used to inoculate 30 ml of NY50 medium with 5 mg/ml BASTA™. After 2 days of growth at 28° C. and 200 rpm, 1.5 ml of each culture was transferred to 30 ml of NYU35 medium without BASTA™ and incubated under the same condition for 4-7 days. Flasks were sampled at 4-7 days and supernatants were assayed for xylanase activity. The three highest xylanase producers were then submitted to Southern analysis to confirm the tri5 gene had been deleted.

Southern hybridizations were performed using the Vistra Kit (Amersham, Arlington, Ill.) and Rapid Hyb Kit (Amersham, Arlington, Ill.) according to the manufacturer's instructions. Fungal genomic DNA from the *Fusarium venenatum* JRoy36-19B putative deletants was prepared using the DNeasy Plant Mini Kit (Qiagen, Chatsworth, Calif.) according to the manufacturer's instructions. One μg of genomic DNA was digested with Sph1 and Dra1 and electrophoresed on an agarose gel. After denaturation and neutralization, the genomic DNA was transferred to a Hybond-N+membrane (Amersham, Arlington, Ill.) using a Turboblotter (Schleicher & Schuell, Keene, N.H.). After prehybridization with Rapid Hyb at 60° C., membranes were hybridized with denatured probe (see below) is overnight at 60° C. Membranes were developed following the manufacturer's instructions and scanned using a STORM 860 (Molecular Dynamics, Sunnyvale, Calif.) according to the manufacturer's instructions.

The "tri5 flanking probe" (fluorecein-labeled, Example 9) hybridized in the 5' flanking region 765 nucleotides upstream of the amdS insertion. The "tri5 open reading frame probe" (fluorecein-labeled, Example 9) hybridized approximately 450 nucleotides downstream of the tri5 ATG.

The results of the Southern hybridization analysis confirmed the deletion of the tri5 gene in the three DAS-negative, high xylanase producing transformants *Fusarium venenatum* LyMC4, LyMC19, and LyMC21. The probe that hybridized to the 5' flanking region of tri5 hybridized to a band corresponding to the size of the deletion construct and did not hybridize to bands corresponding to the native tri5 gene indicated replacement of the region with the deletion construct. Additionally, the probe that bound to the open reading frame of tri5 failed to hybridize in these strains, indicating the loss of the gene.

Example 11

Xylanase Production of *Fusarium venenatum* LyMC4, LyMC19, and LyMC21 Grown with Phosphinothricin Resistance Selection

*Fusarium venenatum* LyMC4, LyMC19, and LyMC21 were subcultured from the original COVE transformation plates described in Example 10 onto plates containing 5 mg/ml of BASTA™ and incubated at 28° C. for 7-10 days. Plugs from the BASTA™ plates of these isolates were used to inoculate triplicate shake flasks according to the protocol for xylanase assays outlined in Example 10. Flasks were sampled at days 4, 5, 6, and 7 and supernatants were assayed.

Xylanase activity was determined as described in Example 6 from samples taken on days 4, 5, 6, and 7 from the flasks. *Fusarium venenatum* LyMC4 and LyMC19 produced xylanase amounts equivalent to or higher than the parental strain *Fusarium venenatum* JRoy36-19B, and these strains were further analyzed.

Example 12

Analysis of High Xylanase-Producing Deletants *Fusarium venenatum* LyMC4 and LyMC19

Single-spore isolates from the two high-producing *Fusarium venenatum* strains LyMC4 and LyMC19 were selected on BASTA™ medium as described in Example 6. Five single-spore isolates of each were maintained on phosphinothricin resistance selection.

Southern hybridization analysis was conducted on the genomic DNA obtained from the five single-spore isolates as described in Example 10.

Southern hybridization confirmed the tri5 gene deletion in all the single-spore isolates. When probed with the fluorescein-labeled probe that binds upstream of the deleted region of the tri5 gene ("Tri5 flanking probe"), all strains had a band corresponding to the size of the deletion cassette, compared to the size of the native tri5 region band of *Fusarium venenatum* JRoy36-19B. The parental strain *Fusarium venenatum* LyMC19 had a faint band corresponding to the wild type tri5 gene, which probably indicated that a small population of nuclei were not deleted. However, all single spore isolates obtained from that strain harbored the deletion. When these same strains were hybridized with the fluorescein-labeled probe that binds to the tri5 open reading frame ("Tri5 open reading frame probe"), only *Fusarium venenatum* JRoy36-19B and *Fusarium venenatum* LyMC19 had bands corresponding to the open reading frame of tri5. The band from *Fusarium venenatum* LyMC19 was very faint and none of the single-spore isolates from that strain had bands, indicating that even before single-spore purification the majority of nuclei were probably deleted of the tri5 gene. The data from both hybridizations indicated that the tri5 open reading frame had been replaced with the amdS deletion cassette in all single-spore isolates.

Example 13

DAS Assays of *Fusarium venenatum* LyMC4- and LyMC19-Derived Strains

The single-spore isolates *Fusarium venenatum* LyMC4.B, LyMC4.C, LyMC19.2, and LyMC19.5, the parental strains *Fusarium venenatum* LyMC4 and LyMC19, and control strains were analyzed for DAS production using the protocols described in Example 10.

All strains were grown in triplicate shake flasks and assayed in the same run. The results of each assay are listed below in Table 1 and the mean DAS yields are shown in the last column. None of the tri5-deleted strains produced detectable amounts of DAS under conditions which induced high DAS levels in a wild type *Fusarium venenatum* strain #93 (BBA 64537, Biologische Bundensanstalt fur Land- und Fortswirtschaft, Berlin, Germany).

TABLE 1

DAS production by single-spore isolates of LyMC4 and LyMC19

| | DAS yield (ppm) | | | mean DAS yield |
|---|---|---|---|---|
| *F. venenatum* Strain | a. | b. | c. | (ppm) |
| #93 | 347 | 355 | 301 | 334 |
| A 3/5[1] | 36 | 15 | 91 | 47 |
| CC1-3 | 29 | 26 | 24 | 26 |
| JRoy36-19B | 24 | 29 | 24 | 26 |
| LyMC4 | 0 | 0 | 0 | 0 |
| LyMC4.B | 0 | 0 | 0 | 0 |
| LyMC4.C | 0 | 0 | 0 | 0 |
| LyMC19 | 0 | 0 | 0 | 0 |
| LyMC19.2 | 0 | 0 | 0 | 0 |
| LyMC19.5 | 0 | 0 | 0 | 0 |

[1]*Fusarium venenatum* Quorn seed vial from Dr. Anthony Trinici, University of Manchester, Manchester, England.

Example 14

Fermentation of *Fusarium venenatum* LyMC4.B, LyMC4.C, LyMC19.2, and LyMC19.5

Fermentations of *Fusarium venenatum* LyMC4. B, LyMC4.C, LyMC19.2, and LyMC19.5 were run at 30° C. for 8 days in 2 liter fermentors containing medium composed per liter of 20 g of sucrose, 2.0 g of $MgSO_4.7H_2O$, 2.0 of $KH_2PO_4$, 2.0 of citric acid.$H_2O$, 2.0 g of $CaCl_2.2H_2O$, 0.5 ml of AMG trace metals (pH adjusted to 4.5 prior to sterilization), and a filter sterilized mixture composed per liter of 2.5 g of urea and 30 ml of a soy vitamin mixture which was added after sterilization and cooling of the medium. Feed streams were batched autoclaved mixtures composed of sucrose and urea.

All of the single-spore isolates produced equivalent amounts of xylanase compared to a similar fermentation of *Fusarium venenatum* JRoy36-19B.

Example 15

Construction of *Fusarium venenatum* N-2

*Fusarium venenatum* strain N-2 was generated from the *Fusarium venenatum* CC1-3 morphological mutant by selection on potassium chlorate medium. The strain was confirmed to possess the niaD phenotype by its ability to grow on 1× Vogels medium supplemented with 2% glucose and 10 mM of either sodium nitrite, ammonium tartrate, hypoxanthine, or uric acid, and its inability to grow on 1× Vogels medium supplemented with 2% glucose and 10 mM sodium nitrate.

Example 16

Construction of the tri5 Deletion Construct pJRoy41 pJRoy40 was digested with BglII and the ends were filled in with the Klenow fragment according to Sambrook et al., 1989, supra. The linearized vector was purified by 1% agarose gel electrophoresis using TAE buffer and agarase treatment. The vector was next treated with calf intestinal alkaline phosphatase according to Sambrook et al., 1989, supra. The nit3 gene of *Neurospora crassa* was removed from pNit3 (Fu and Marzluf, 1987, supra) by digestion with Not1 and SrtI. The restriction reaction was treated with the Klenow fragment, and subjected to 1% agarose gel electrophoresis using TAE buffer. The 4886 bp fragment containing the nit3 gene was isolated using agarase.

Figure 8:
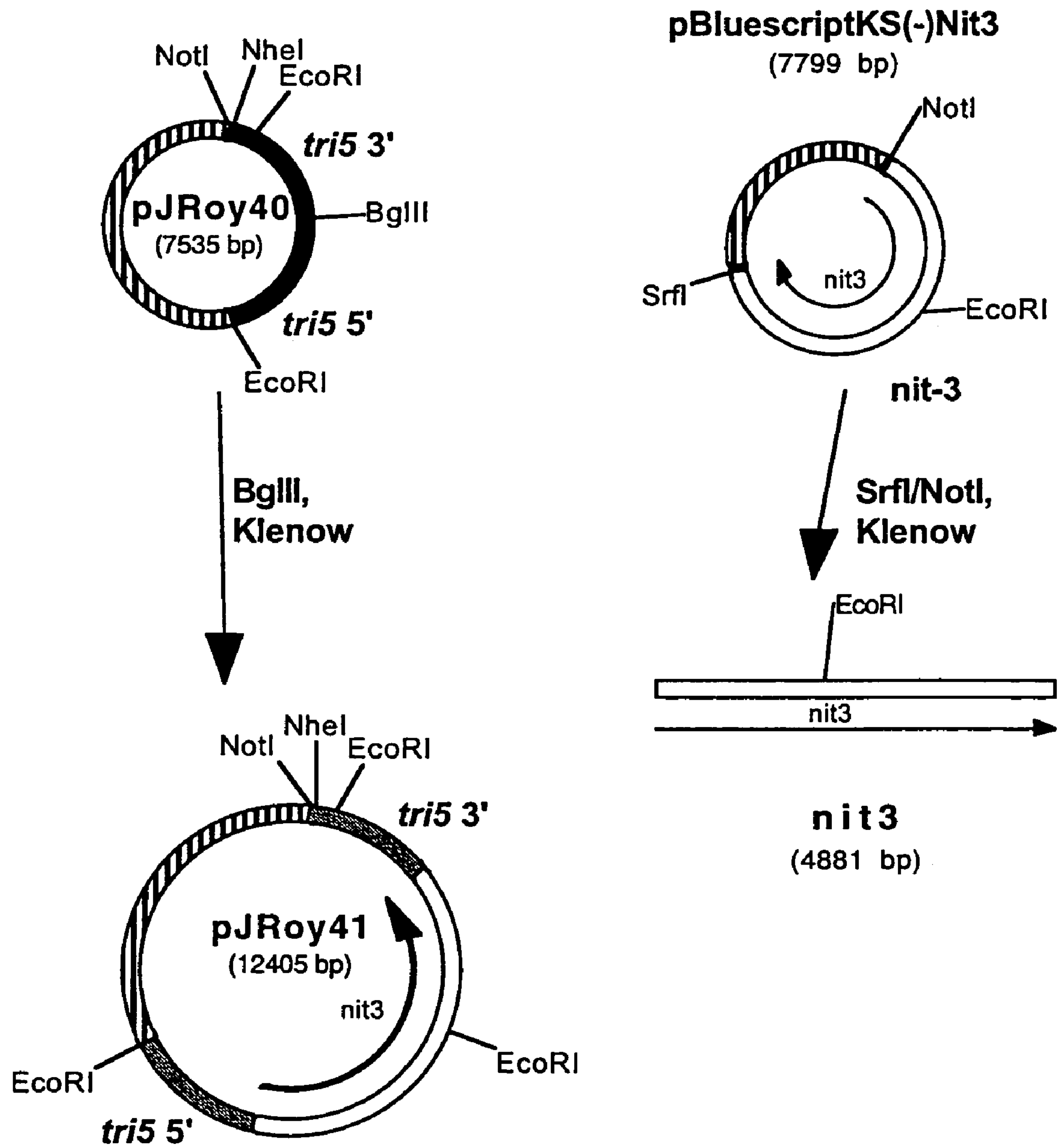
FIG. 8 shows the construction of pJRoy41.

The nit3 gene fragment was cloned into the filled in BglII site of pJRoy40 to create pJRoy41 (FIG. 8). In this vector, the 3.7 kb fragment containing the tri5 gene in the *Fusarium venenatum* genome was replaced with the 4.9 kb fragment containing the *Neurospora crassa* nit3 gene.

Example 17

Transformation of *Fusarium venenatum* N-2 and Analysis of Transformants

Biomass for generation of protoplasts of *Fusarium venenatum* N-2 was prepared in 2 different ways. For batch 1, 50 ml of YEPG medium were inoculated with 5 agar plugs (1 cm) of *Fusarium venenatum* N-2, and cultured for 3 days at 26° C. and 150 rpm. Ten ml of this culture were used to inoculate another 100 ml culture of YEPG, which was incubated at 200 rpm, 28° C. for 20 hours before protoplasting. For preparation of Batch 2 protoplasts, agar plugs of *Fusarium venenatum* N-2 were inoculated into RA sporulation medium containing 0.1M $Na_2HPO_4$ and 0.1 M $NH_4H_2PO_4$, instead of sodium nitrate, plus 0.05% glucose. The culture was grown for 4 days at 28° C. and 200 rpm. Fernbach flasks containing 500 ml of medium composed per liter of 10 g of succinic acid, 0.1 M $NH_4H_2PO_4$, 0.1M $K_2HPO_4$, 1× COVE salts, and 0.5 g of glucose were inoculated with 10 ml of the first culture, and incubated for 65 hours at 26° C. and 150 rpm. Approximately $10^8$ spores were obtained from this culture. The spores were used to inoculate 50 ml of YEPG medium, which were grown for 13.5 hours at 24° C. and 150 rpm. Protoplasts were prepared as described in Example 6 and stored at −80° C.

Protoplasts of *Fusarium venenatum* N-2 were transformed with pJRoy41 (either uncut, linearized at the Not1 site in the polylinker, or linearized at the NheI site in the 3' flank). Transformations were performed with pJRoy41 as described in Example 6, except that the reactions were plated onto empty 150 mm plates with 50 ml of (40° C.) overlay medium containing 1× COVE salts , 0.8 M sucrose, 25 mM sodium nitrate, and 1% low melt agarose.

Four transformants were obtained from NotI digested pJRoy 41, 2 were obtained from NheI digested pJRoy 41, and 32 were obtained from undigested plasmid.

Example 18

Genomic DNA Preparation of Putative *Fusarium venenatum* tri5 Deleted Transformants Genomic DNA was prepared from the putative *Fusarium venenatum* tri5 deleted transformants described in Example 17 using the following protocol. The transformants were grown in 25 ml of YEG medium for 72 hours at 30° C. and 250 rpm. Mycelia were then collected by filtration through Miracloth and washed once with 25 ml of 10 mM Tris-1 mM EDTA (TE) buffer. Excess buffer was drained from the mycelia which were subsequently frozen in liquid nitrogen. The frozen mycelia were ground to a fine powder in an electric coffee grinder, and the powder was added to 20 ml of TE buffer and 5 ml of 20% w/v sodium dodecylsulfate (SDS) in a disposable plastic centrifuge tube. The mixture was gently inverted several times to insure mixing, and extracted twice with an equal volume of phenol:chloroform:isoamyl alcohol (25:24:1 v/v/v). Sodium acetate (3 M solution) was added to a final concentration of 0.3 M followed by addition of 2.5 volumes of ice cold ethanol to precipitate the nucleic acids. The nucleic acids were then pelleted by centrifuging the tube at 15,000×g for 30 minutes. The pellet was allowed to air dry for 30 minutes before resuspension in 0.5 ml of TE buffer. DNase-free ribonuclease A was added to a concentration of 100 mg/ml and the mixture was incubated at 37° C. for 30 minutes. Proteinase K was then added at a concentration of 200 mg/ml and the mixture was incubated an additional hour at 37° C. Finally, the mixture was extracted twice with phenol:chloroform:isoamyl alcohol (25:24:1 v/v/v) before precipitating the DNA with sodium acetate and ethanol as described earlier. The DNA pellet was dried under vacuum, resuspended in TE buffer, and stored at 4° C. until further use.

Example 19

PCR Screen for Deletion of the tri5 Gene

A preliminary PCR screen was performed to test for deletion of the tri5 gene in the transformants isolated in Example 17. The reaction was designed using primers that would amplify a 1.1 kb band from intact tri5 DNA, but would fail to generate a band from DNA in which the tri5 coding region had been replaced with the nit3 gene. The PCR reaction was carried out with primers 551 5'-CGGTATCGAATGTACTCGAG-3' (Tri5 bp 2524-2544) (SEQ ID NO. 16) and 510 5'-CCCATGGTGTGAACACC-3' (tri5 bp 1397-1414) (SEQ ID NO. 17). The reaction contained 2.5 μl of DMSO, 1 μl of Taq DNA polymerase, 5 μl of 2.5 mM each of dATP, dCTP, dGTP, and dTTP, 5 μl of 10× PCR buffer, 0.5-1 μg of transformant genomic DNA (Example 18), 2 μl of each primer above at 50 pmol/μl, and the appropriate amount of water to obtain 50 μl. The reaction was performed using 1 cycle at 97° C. for 5 minutes, 55° C. for 1 minute, and 72° C. for 1 minute, followed by 30 cycles each at 97° C. for 1 minute, 55° C. for 1 minute, and 72° C. for 1 minute.

Transformants which failed to generate a 1.1 kb band corresponding to an intact tri5 gene were cultured in liquid Vogels medium supplemented with 25 mM $NaNO_3$ and subjected to DAS analysis as described in Example 10. Several transformants produced no measurable levels of DAS under these growth conditions, while the positive control consistently produced approximately 10 ppm DAS (Table 2).

TABLE 2

Summary of DAS and Southern analysis for putative tri5 deletants

| Strain | DAS (ppm) | tri5 5' probe | tri5 orf probe |
|---|---|---|---|
| CC1-3 | 10 | 5.9 | + |
| N2-119 | ND | 5.9 | + |
| N2-1 | ND* | 7.1 | − |
| N2-8 | ND | 7.1 | − |
| N2-13 | ND | 7.1 | − |
| N2-103 | ND | 7.1 | − |
| N2-106 | ND | 7.1 | − |
| N2-118 | ND | 7.1 | NT** |
| N2-101 | 11 | 5.9, 7.1 | + |

TABLE 2-continued

Summary of DAS and Southern analysis for putative tri5 deletants

| Strain | DAS (ppm) | tri5 5' probe | tri5 orf probe |
|---|---|---|---|
| N2-102 | 19 | 5.9, 7.1 | + |
| N2-104 | 18 | 5.9, 7.1 | + |
| N2-105 | 35 | 5.9, 7.1 | + |

*ND: not detectable
**ND: not tested

The strains which failed to generate a 1.1 kb band in the diagnostic PCR reaction were also subjected to Southern analysis. Putative *Fusarium venenatum* tri5 deleted strain genomic DNA prepared as described in Example 18 was restriction digested with DraI/SphI. The fragments were separated by electrophoresis on a 1% agarose gel using TAE buffer. DNA was transferred overnight to a Nytran Plus membrane using 5×SSC as the wicking buffer. The membrane was prehybridized for 2 hours at 65° C. in DIG Easy Hyb. Hybridization was performed with the DIG-labeled "tri5 flanking probe" (Example 9). Subsequently, the membrane was washed twice for 15 minutes each at room temperature in 2×SSC-0.1% SDS followed by two washes for 15 minutes each at 68° C. in 0.1×SSC-0.1% SDS. The washed membrane was developed according to standard DIG protocol and exposed to Kodak X-OMAT AR film for approximately 1 hour at room temperature followed by development using a Konica QX-70 automatic film processor according to the manufacturer's instructions.

Genomic DNA digested with DraI/SphI contained a 5932 bp hybridizing band in the wild type strain, and a 7100 bp hybridizing band in the deletion plasmid when the DIG-labeled "tri5 flanking probe" was utilized. The 5.9 kb band corresponded to the wild type tri5 gene, while the 7.1 kb band corresponded to DNA where the nit3 gene had replaced the tri5 gene. Several transformants produced two bands corresponding to both the intact tri5 gene and to the deletion plasmid. In these strains, the deletion integrated ectopically, resulting in no deletion of the tri5 gene. However, *Fusarium venenatum* transformants N2-1, N2-8, N2-113, N2-103, N2-106, and N2-118 each contained the single 7.1 kb band indicative of the deletion plasmid.

Genomic DNA from these putative deletants was also hybridized with the DIG-labeled "tri5 open reading frame probe" (Example 9). In all but one case, the strains which displayed a single band indicative of the deletion plasmid during hybridization with the 5' probe failed to contain a band which hybridized with the open reading frame probe of tri5. From Table 3, the majority of strains which were identified as tri5 deletants by DAS analysis were identified as tri5 deletants by Southern analysis. The data indicated that *Fusarium venenatum* strains N2-1, N2-8, N2-113, N2-103, and N2-106 were deleted in the tri5 gene.

Example 20

Generation of a nit3 Marker-Free tri5 Deletion in *Fusarium venenatum* Strain

Removal of the nit3 gene from the deletant *Fusarium venenatum* N2-8 was accomplished by transforming the strain with an EcoRI fragment containing the 5' and 3' flanking DNA from the deletion construct pJRoy40 (Example 7). Protoplasts and transformations were performed as described in Example 10. Transformation reactions were allowed to regenerate for 24 hours at room temperature after addition of 10 ml of YEPG medium supplemented with 0.8 M sucrose as osmoticum. The regenerated protoplasts were then concentrated and washed in sterile water by centrifugation (10 minutes, 2000×g) and plated on potassium chlorate medium at a density of $5\times10^6$ per ml. Several hundred colonies grew on the chlorate medium. One hundred of these colonies were analyzed based on their ability to grow on sodium nitrite, ammonium tartrate, hypoxanthine and uric acid, and their inability to grow on sodium nitrate. Approximately 50 niaD mutants were identified.

Twenty of these mutants were subjected to Southern analysis using the "tri5 flanking probe" as described in Example 9. One transformant (N2-8-1) contained a band indicative of loss of the nit3 gene. Southern hybridization was repeated with the niaD mutant (N2), the nit3/tri5 replaced strain N2-8, and the putative excised strain N2-8-1. DNA from these strains was digested with NheI and NruI and probed with the "tri5 flanking probe". The results showed the presence of a 6436 bp band in the N2 strain which was consistent with a wild type tri5 gene, and the presence of a 7604 band in the nit3/tri5 replaced strain N2-8 which was consistent with the replacement of the tri5 gene with nit3. There was a decrease in size of the hybridizing band to 2718 bp in the excised strain N2-8-1 which was consistent with excision of the nit3 gene.

Example 21

Generation of an amdS Marker-Free tri5 Deletion in *Fusarium venenatum* Strain MLY3

An unmarked tri5 deletion in the genome of the *Fusarium venenatum* expression host MLY3 was generated as shown in FIG. 9 by initially deleting the tri5 gene and replacing it with the amdS gene flanked by repeated DNA sequences isolated from the upstream region of the *Aspergillus oryzae* pyrG gene (WO 98/12300). Isolates cured of the amdS gene were then selected by growth on plates containing fluoroacetamide.

Plasmid pLC31b was constructed by introducing direct repeats at the flanks of the *Aspergillus nidulans* amdS gene, and subcloning the resulting amdS cassette into the tri5 deletion vector pJRoy40 (Example 5).

The initial step was the creation of pJRoy43, which is composed of pNEB193 (New England Biolabs) where the PacI and XbaI sites were replaced with a SwaI site. To accomplish this, a linker containing a BamHI site on the 5' end, a SwaI site in the middle, and a SalI site on the 3' end was created by annealing the following two oligos together:

```
5'-GATCGATTTAAAT-3'      (SEQ ID NO. 18)
5'-TCGAATTTAAATC-3'      (SEQ ID NO. 19)
```

The resulting linker was ligated into pNEB193, which had been digested with BamHI and SalI, to create pJRoy43.

Next, a 230 bp region upstream of the *Aspergillus oryzae* pryG gene was chosen as a repeat sequence in *Fusarium venenatum*. This region was amplified as two different products from the *Aspergillus oryzae* pyrG plasmid pJaL335 (WO 98/12300) using the following two primer pairs, primers 3 and 4 and primers 5 and 6:

Primer 3: 5'-CGAATTTCATATTTAAATGCCGACCAGCAGACGGCCCTCG-3' (SEQ ID NO. 20)

Primer 4: 5'-GCGATATCATGATCTCTCTGGTACTCTTCG-3' (SEQ ID NO. 21)

Primer 5: 5'-GCGATATCATCGACCAGCAGACGGCCCTCG-3' (SEQ ID NO. 22)

Primer 6: 5'-GCGTTTAAACATGATCTCTCTGGTACTCTTCG-3' (SEQ ID NO. 23)

The amplification reactions (50 μl) were prepared using approximately 40-50 ng of genomic DNA, prepared using the DNeasy Plant Mini Kit, as the template. Each reaction contained the following components: 40-50 ng of genomic DNA, 50 pmol each of the primers 3 and 4 or primers 5 and 6, 200 μM each of dATP, dCTP, dGTP, and dTTP, 1× Taq DNA polymerase buffer, and 2.5 Units of Taq DNA polymerase. The reactions were incubated in a Perkin-Elmer Model 480 Thermal Cycler programmed as follows: Cycle 1 at 94° C. for 2.5 minutes and 72° C. for 2.5 minutes; cycles 2-26 each at 94° C.for 45 seconds, 50° C. for 45 seconds, and 72° C. for 2 minutes; and cycle 27 at 94° C. for 45 seconds, 50° C. for 45 seconds, and 72° C. for 10 minutes.

The reaction products were isolated on a 1% agarose gel where approximately 230 bp fragments were isolated. The first PCR product (approximately 230 bp fragment) contained a SwaI site at the 5' end and an EcoRV site at the 3' end while the second PCR product (approximately 230 bp fragment) contained an EcoRV site at the 5' end and a PmeI site at the 3' end. The two purified repeat fragments were first digested with EcoRV and ligated together. After purification (phenol-chloroform etraction and ethanol precipitation), the ligation product was then digested with PmeI and SwaI to produce approximately a 500 bp fragment which was purified by agarose gel electrophoresis and agarase treatment.

Figure 10:
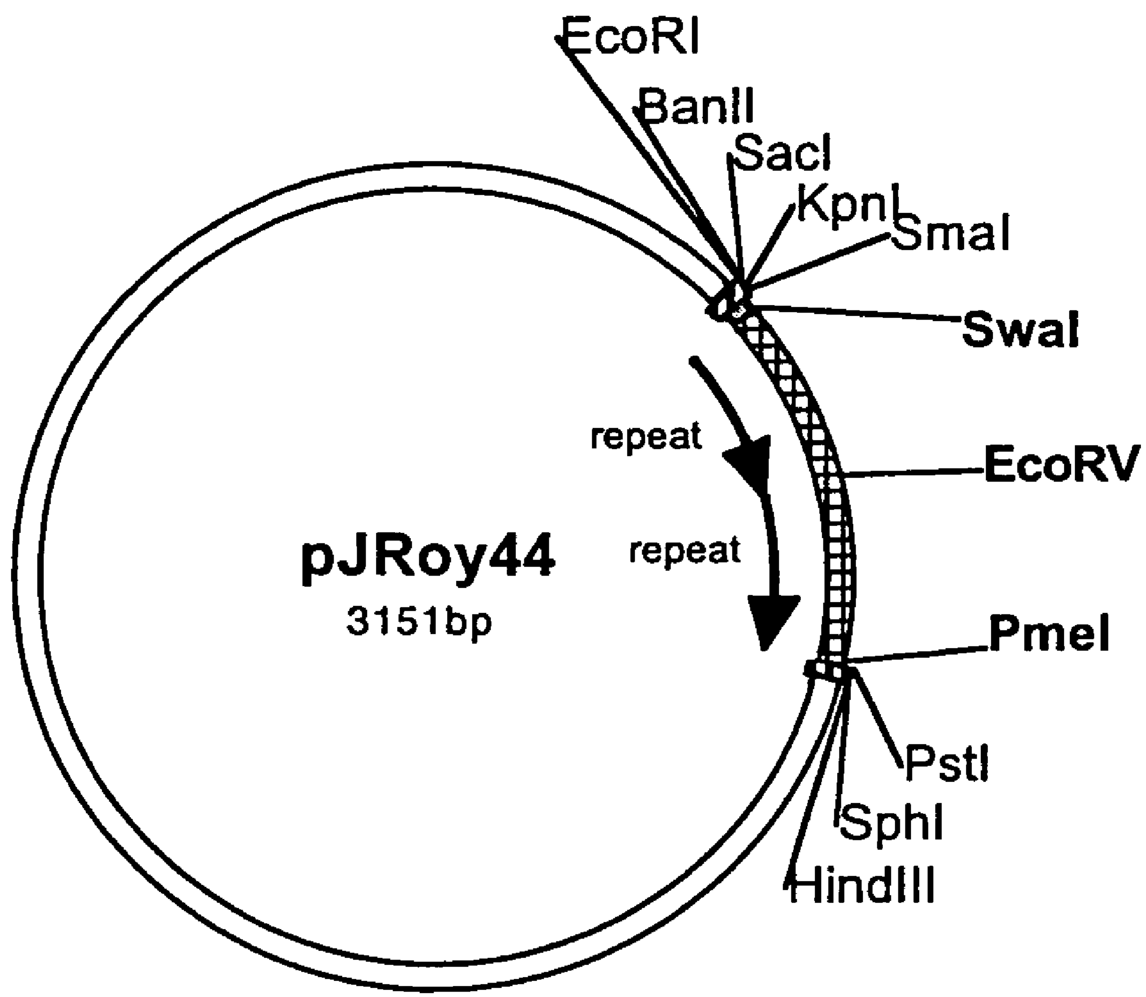
FIG. 10 shows a restriction map of pJRoy44.

The resulting fragment was cloned into PmeI and SwaI digested pJRoy43 to create pJRoy44 (FIG. 10). This vector contains the two 230 bp repeats separated by an EcoRV site and flanked by SwaI and PmeI sites.

Figure 11:
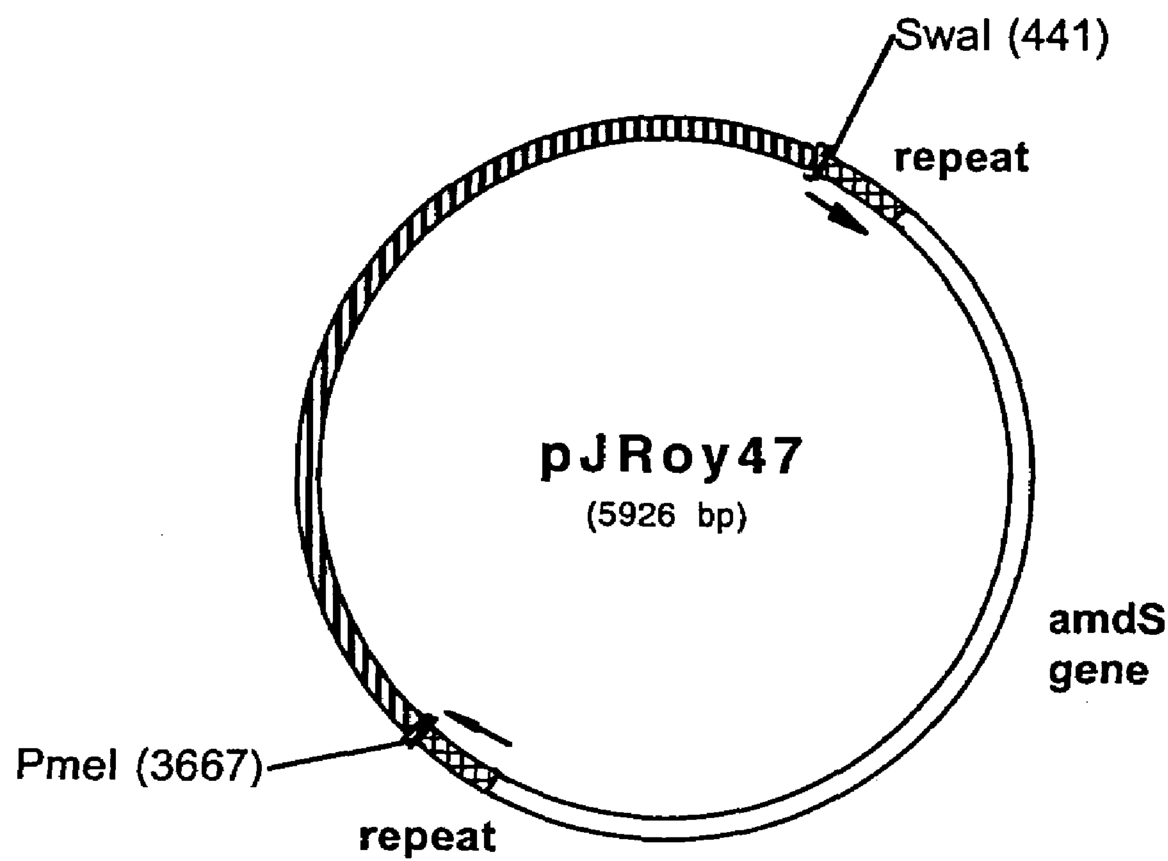
FIG. 11 shows a restriction map of pJRoy47.
Figure 12:
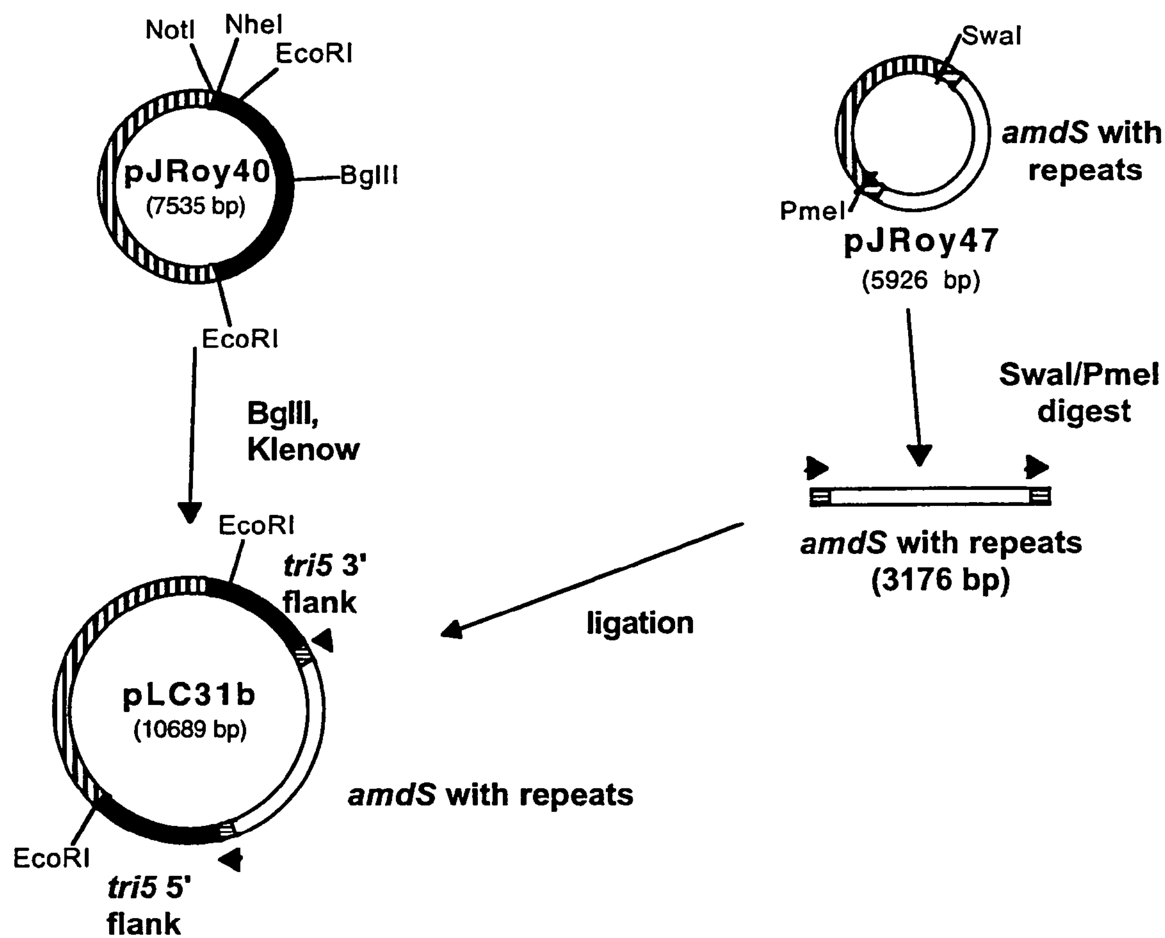
FIG. 12 shows the construction of pLC31b.

An EcoRI fragment containing the amdS gene and regulatory region was isolated from a subclone of p3SR2 (Kelly and Hynes, 1985, *EMBO Journal* 4: 475-479), made blunt with the Klenow fragment, and ligated into EcoRV digested pJRoy44 to create pJRoy47 (FIG. 11). This vector was digested with PmeI and SwaI, and the fragment containing the amdS gene flanked by the direct repeats described above was ligated into BglII digested, Klenow treated JRoy40 to create pLC31b (FIG. 12) where the 3.7 kb fragment containing the tri5 coding region had been replaced with the 3 kb fragment containing the *Aspergillus nidulans* amdS gene flanked by 230 bp repeats.

The resulting plasmid, pLC31b, was then digested with EcoRI and the 6.1 kb EcoRI fragment containing this tri5 deletion cassette was gel purified using Qiaquick Gel Extraction Kit (Qiagen, Chatsworth, Calif.) prior to transformation.

*Fusarium venenatum* MLY3 protoplasts were prepared and then transformed as described in Example 6 with the gel-purified 6.1 kb EcoRI deletion fragment. Transformants were plated onto COVE plates to select for integration of the amdS gene. Replacement of the native tri5 gene with the deletion cassette was confirmed by Southern hybridization in the 3 resulting transformants. Southern hybridizations were conducted using the Amersham (Arlington, Ill.) Vistra and Rapid Hyb protocols or the Boehringer Mannheim DIG System protocol provided by the manufacturer. Fungal genomic DNA of putative deletants was prepared using the DNeasy Plant Mini Kit (Qiagen Chatsworth, Calif.). Membranes were developed following the manufacturer's instructions and scanned using a STORM 860 (Molecular Dynamics, Sunnyvale, Calif.) for fluorescein-labeled probes or exposed to film for DIG-labeled probes. The "tri5 flanking probe" hybridizes in the 5' flanking region 765 nts upstream of the amdS insertion.

All three transformants were sporulated and single spores were isolated using a micromanipulator. Three of the single-spore isolates of the three deleted transformants (9 total strains) were again sporulated. Selection for loss of the amdS marker occurred by spreading $1\times10^6$ spores of the confirmed tri5 deletants onto each of nine 150 mm plates containing fluoroacetamide medium. These plates were incubated at room temperature for up to 2 weeks. Resulting colonies were subcultured onto COVE plates and new fluoroacetamide plates. Colonies that grew well on fluoroacetamide and poorly or not at all on COVE were analyzed further. Of 308 isolates able to grow on fluoroacetamide ($FA^+$), 3 were unable to grow on COVE ($COVE^-$) and 1 grew very poorly on COVE but well on fluoroacetamide. Southern hybridization showed that the 3 $COVE^-$ strains still contained the amdS gene, while the one showing poor growth on COVE had a band corresponding to the predicted size of a "loop-out". This deletant, designated LyMC1, was sporulated and 3 isolates derived from single spores were obtained. The results of the Southern blots confirmed deletion of tri5 and loss of the amdS gene in one transformant and in three spore-purified isolates derived from that transformant, LyMC1A, LyMC1B, and LyMC1C. Spores of all three transformants were generated as described in Example 6, except that Vogels nitrate medium was used and cultures were incubated for 72 hours at 24° C. Single spores were isolated using a micromanipulator.

Homologous recombination between the repeated sequences should result in deletion of the complete amdS gene. To confirm complete loss, the deletion region was PCR amplified using the following primers that hybridize to the 3' and 5' flanking regions of the tri5 gene:

GAGa3.3: 5-GGTAGCACGAGTGTCTGG-3' (SEQ ID NO. 24)

Tox5': 5'-AACTGGAAAGACCTGTGGGC-3' (SEQ ID NO. 12)

The amplification reactions (50 μl) were prepared using approximately 40-50 ng of genomic DNA of each deletant, prepared using the DNeasy Plant Mini Kit, as the template. Each reaction contained the following components: 40-50 ng of genomic DNA, 50 pmol of the forward primer, 50 pmol of the reverse primer, 200 μM each of dATP, dCTP, dGTP, and dTTP, 1× Taq DNA polymerase buffer, and 2.5 Units of Taq DNA polymerase. The reactions were incubated in a Perkin-Elmer Model 480 Thermal Cycler programmed as follows: Cycle 1 at 94° C. for 2.5 minutes and 72° C. for 2.5 minutes; cycles 2-26 each at 94° C. for 45 seconds, 50° C. for 45 seconds, and 72° C. for 2 minutes; and cycle 27 at 94° C. for 45 seconds, 50° C. for 45 seconds, and 72° C. for 10 minutes.

The reaction products were isolated on a 1% agarose gel where a 990 bp product band was excised and cloned into pCR2.1 from the TOPO TA Cloning Kit (Invitrogen, Carlsbad, Calif.) following the manufacturer's instructions, then used to transform One Shot TOP10 cells (Invitrogen, Carlsbad, Calif.). DNA was prepared from the resulting transformants using a Qiagen QIAprep-8 kit and analyzed by restriction digest using EcoRI. Plasmids were sequenced on an ABI PRISM 377 DNA Sequencer (ABI, Foster City, Calif.). PCR-amplification and sequencing of the deletion region demonstrated that a complete loop-out occurred and that only a single 230 bp repeat remained at the tri5 locus. This repeat contained the 5' end of the 5' repeat and the 3' end of the 3' repeat, indicating that homologous recombination had occurred between the 2 repeats.

DAS production from the 3 spore-purified deletants, *Fusarium venenatum* MLY3, and wild type *Fusarium venenatum* strain BBA 64537 was determined as described in Example 10, except that Vogels nitrate medium was used to generate spores. Table 3 shows the DAS results from this analysis. None of three tri5 deletants, LyMC1A, LyMC1B, or LyMC1C, produced any detectable DAS, while the wild type *Fusarium venenatum* strain BBA64537 and *Fusarium venenatum* MLY3 produced detectable amounts of DAS.

TABLE 3

DAS Analysis of tri5 deleted *Fusarium venenatum* strains

| Strain | DAS (ppm)* Mean of 3 values (+/−S.E.) |
|---|---|
| BBA 64537 | 318 (+/−31) |
| MLY3 | 29 (+/−11) |
| LyMC 1A | <2 |
| LyMC 1B | <2 |
| LyMC 1C | <2 |

*Detection limit 2 ppm.

DEPOSIT OF BIOLOGICAL MATERIAL

The following biological material has been deposited under the terms of the Budapest Treaty with the Agricultural Research Service Patent Culture Collection, Northern Regional Research Center (NRRL), Peoria, Ill., and given the following accession numbers:

| Deposit | Accession Number | Date of Deposit |
|---|---|---|
| *E. coli* DH5α pTri5 | NRRL B-30029 | May 6, 1998 |

The strain has been deposited under conditions that assure that access to the culture will be available during the pendency of this patent application to one determined by the Commissioner of Patents and Trademarks to be entitled thereto under 37 C.F.R. §1.14 and 35 U.S.C. §122. The deposit represents a substantially pure culture of the deposited strain. The deposit is available as required by foreign patent laws in countries wherein counterparts of the subject application, or its progeny are filed. However, it should be understood that the availability of a deposit does not constitute a license to practice the subject invention in derogation of patent rights granted by governmental action.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosures of which are incorporated by reference in their entireties.

What is claimed is:

1. A method for obtaining a mutant *Fusarium venenatum* cell, comprising:

(a) introducing into an endogenous gene of the genome of a parent *Fusarium venenatum* cell, a nucleic acid construct comprising a nucleic acid sequence of the endogenous gene inactivated with a nitrate reductase gene to produce a mutant *Fusarium venenatum* cell comprising an endogenous gene incapable of expressing the endogenous gene product wherein the endogenous gene is one or more genes selected from the group consisting of a tri3 gene, a tri4 gene, a tri6 gene, a trill gene, a tri12 gene, and a tril01 gene;

(b) selecting the resulting mutant *Fusarium venenatum* cell from step (a) for the presence of the nitrate reductase gene and loss of production of the gene product;

(c) introducing into the mutant *Fusarium venenatum* cell from step (b) a second nucleic acid construct comprising a second inactivated nucleic acid sequence of the endogenous gene comprising 5' and 3' regions of the inactivated nucleic acid sequence of the endogenous gene, but lacking the nitrate reductase gene, wherein the second nucleic acid construct incorporates into the genome of the mutant *Fusarium venenatum* cell replacing the inactivated nucleic acid sequence and is incapable of expressing the endogenous gene product; and (d) selecting a mutant *Fusarium venenatum* cell from step (c) in the absence of the nitrate reductase gene.

2. The method of claim 1, further comprising introducing into the parent *Fusarium venenatum* cell a nucleic acid construct comprising a tri5 gene inactivated with the nitrate reductase gene.

3. The method of claim 1, wherein the endogenous nucleic acid sequence is a tri3 gene.

4. The method of claim 1, wherein the endogenous nucleic acid sequence is a tri4 gene.

5. The method of claim 1, wherein the endogenous nucleic acid sequence is a tri6 gene.

6. The method of claim 1, wherein the endogenous nucleic acid sequence is a tri11 gene.

7. The method of claim 1, wherein the endogenous nucleic acid sequence is a tri12 gene.

8. The method of claim 1, wherein the endogenous nucleic acid sequence is a tri101 gene.

* * * * *

SEQUENCE LISTING

```
<160> NUMBER OF SEQ ID NOS: 24

<210> SEQ ID NO 1
<211> LENGTH: 6946
<212> TYPE: DNA
<213> ORGANISM: Fusarium

<400> SEQUENCE: 1

gaattctctc agtcggcctc atctggcagg tgctaatata ttctacccgc gcttggctac     60

ctatgccaca cacaaagctt catgtttggt tcatatcgta tactcgcttc aacagttctg    120

cgggtacgac tctcgtatgg atgtaataaa caaatgttcc gacctattat gccgagttac    180

cgtggacaat tatcgggccg gaaaagaatg catttgtgaa ttgtaatcct gcctgtttgt    240

ggagtgataa gtgacatatt ggaaaagtcg tcaagcaatt ggaggtttca tcaactgtgg    300

agtcatcgtt ttgggcaaac aatactatgt agggtaggct tctgctgcag catcaatgac    360

tcgtttggat cgagtccttt tgttgccaag gcgtatgggg cctgcaggga acgagtcagt    420

cgtatcaggc cggtgaggca aatgccgttt cgcagcagct atcatttgtc gcgggatttt    480
```

-continued

```
cgcgaagctt tgcgtgacga gtcaaatccg cacatcttga ttcatgagtt gttgaattta    540
gctgttcatt cgtgagtggc taaagcgtat ctagtcgatt gtcaaattca gacttgacag    600
gtcccttgat gaatgagacg tcggatgtcc ctagccgaga tgcggattgt gacaacggaa    660
gagacagggg cagggttcat gggtgttgaa ccttgttcac tgaaacggtg atgtctttgg    720
tctacaaagt atccttcaca tgtctctgtt cccagaccac gtggttattc tggcatccgg    780
gtcctattga ttggctgatt tcttgcactg atacatacaa ataagtccaa gactgtattc    840
tactggcaaa attatgccga caaggggaaa tcattctgaa ttagtgatga agcatgccgt    900
cgaagccgaa gagaaacttt gcgcagcaac tggaaagacc tgtgggctgt agagcgcaca    960
gcacggtagt aagacctacg gccctggtat catggttgta gcctcttccg tattgctcac   1020
atatccaccg gttttctaca taaacagtct gagtcctgat agtggatatt atatcttcca   1080
ggacctagtc taggtagtag tcggcatttg aaacgcctag tggcaagaga tcgcttagcc   1140
tccagcctgg caatatcgcg gcttcctcag gttgtaccac gaatgatgat ctcaattgtg   1200
cttcccctgt cgtgaatttg ctagtgcgac gggacttgcc aggcttacgg cacctacaag   1260
tcgcgccagc cttctgacag tgattgtatg caagatcgtc attagttatg attaagcttt   1320
gataaacaag agcgccacag cctttcttta actccgacaa cctcaacggt gacatgcata   1380
ccgcgtgaca ctatttccca tggtgtgaac accatcaatg acttagagta gataaccact   1440
tgaaacttct agaaatgtcc aagaaactac actcagtgtt tcatagaact aagacaatgt   1500
tcattgaagg atgggatttg agactccgta ctgcttcacc tcggaaaata agcactgttt   1560
agcacccgtt aagccaagtc cttcaaacgt ggggacggat ttaaccaaca gcagagtgga   1620
taagcctgta ctctactcat tgaatgtata taatacattg ctaggtacat acgcagcttt   1680
caggcacaga taacgaagat cttagggtag attccaaaac atcggaaggg gtcacagatc   1740
gcactagcta ctatgccatc cagagcctct tgctaaccaa acagagctaa gtcgcttaac   1800
ccttattcaa agaacacagt tgtattgtgc atccgggatc taactgtctt ggacaagcgt   1860
gttctgtatc cgtaacggct ggtggttttg tagggtatga tagaatggtt gcacttaagg   1920
cctgtcgact aggtaagctt ttcccaggga agaataaaac accgcggctg cttagacaag   1980
tgaggctttc ttctccgtca acaaactgcc gtctcactag tccaaacttg gtcacggaca   2040
acagccgaac tcaaacattt agcctcagga ttcatcccta gctttaggcc tactcctcgt   2100
cccttgacac cgggatgtag ttcctatcgc ttgcgtagct ctttactgca tgtgccgagc   2160
taaagataaa atcggactaa agattcgttc cgggagccga atgctttctc aagctcgtcg   2220
tgttgcaggg gatggaagac ctccagcgta cgtcacggtc tctatcacta cgaatttgct   2280
gggaaggcta tttgcattaa tgtcaagtca attattaggc ctaacaacac aagtttaact   2340
aaagattgtg gatggttgac atttgccata tgttgatata tagttgatag caacagcact   2400
ttgcaatagg acaataatag cgacttgact tgaaaattcg caaagaactg ttataaatca   2460
ttataccatt atcatcatgg agaactttcc cactgagtat tttctcaaca cttctgtgcg   2520
ccttctcgag tacattcgat accgagatag caattatacc cgggaagagc gtatcgagaa   2580
tttgcactat gcttacaaca aggctgctca tcactttgct cagccacgac aacagcagct   2640
gctcaaggta gaccctaagc gactacaggc ttccctccaa actattgttg gcatggtggt   2700
atacagttgg gcaaaggtct ccaaagagtg tatggcggat ctatctattc attacacgta   2760
cacactcgtt ttggatgaca gcagcgatga tccgtatcca gccatgatga actatttcaa   2820
cgatcttcag gctggacgag aacaggccca cccatggtgg gcgcttgtta atgagcactt   2880
```

-continued

```
tcccaatgtc cttcgacatt ttggtccctt ctgctcattg aaccttatcc gcagcactct   2940
tgactgtaag taccctggct ctattatttc accgccttaa taagctaaca gtgatggaat   3000
tatagttttt gagggatgct ggatcgagca gtacaacttt ggaggatttc caggatctca   3060
tgactatcct cagtttcttc gacgcatgaa tggcttgggt cactgtgtcg gggcttcttt   3120
gtggcccaaa gagcagtttg atgagagagg tctattcctt gaaatcacat cagccattgc   3180
tcagatggag aactggatgg tctgggtcaa tgatctcatg tctttctaca aggagttcga   3240
tgatgagcgt gaccagatca gtctcgtcaa gaactacgtc gtctctgatg agatcactct   3300
ccacgaagct ttagagaagc tcacccagga cactctacac tcgtccaagc agatggtagc   3360
tgtcttctct gacaaggacc ctcaggtgat ggacacgatt gagtgcttca tgcacggcta   3420
tgtcacgtgg cacttgtgcg atcacaggta ccgtctgaat gagatctacg aaaaggtcaa   3480
aggacaaaag accgaggacg ctcagaagtt ctgcaagttc tatgagcagg ctgctaacgt   3540
cggagccgtt tcgccctcgg agtgggctta tccacctatt gcgcaactgg caaacattcg   3600
gtccaaggat gtgaaggatg tgaaggatgt gaaggagatt cagaagcctc tgctgagctc   3660
aattgagcta gtggaatgac cgacggtgag atggaagtat gttttgcggg tactcgctag   3720
gagaatactg gtcgtttatc atgattacaa atagcttggt tatgttttta ttagcattta   3780
cagttgaaca aggataatta ctactgaata ggcagctgaa actgatgtct gtaactccag   3840
cctgttattc cacttgcctg caggtctttg catggccaag tcatacatac ctgttacggt   3900
gtcggtgcga cagggctatc catacccccgg cccagcctgc agtagagcag gcgtcacggc   3960
ctgtagtgcg ctgcgggaat cttccacccg ttcggatgtg ggaagttttg ttgtcctcgg   4020
ggctaacaca ttccaaccat taattgatct tcaaaacgct tgcatttgct ctatatggcc   4080
ggccttgatc cttgtatatt ttcaccatct gacattttct gcacaaggcg tacagaaacc   4140
acacgaggta aagtttcatg gccgcttggc cactattgga aacacgacac acatgttaaa   4200
ctctatcctt gcattatatt gtaacatcgc ctaacatctc cacgcactat tcctttgcgt   4260
tccttattca tcctcaactg tatgccaacc aacaatcatc aaattattat tgcagttagt   4320
catcatggat ttcccaaagc cgaggcaggt tagagagacg agcctgttga tgtactacct   4380
ggacgtcgtg ttttctctac aatgcattac cccaaacaac aattgtctgg gcaagagaga   4440
gtggctgttg actatactaa cctctgctcg gcctacgtac tatgcaacat tgtgcctggc   4500
cctcctttat aaagaatccc tctcaagccc ttgcagagcc gaacaagcgg tagtatggaa   4560
gagagaaaag acctactact acattcttgc gctccaagag tctcagaagc tgttgggtgg   4620
actcgacaag acttttggta tcacaaggct gaaggggacc gtcgttgccc ttgcttgcat   4680
gatccagctc atcgggtttg aggtaagacg aatccacaac gctcacaatg ttcaataccc   4740
gatctataat tatcattgga gactaacgca tttggacagt cttcgcactt aagtagggga   4800
gattggcgcg ttcacctcct tgcagccaac acactcattc ctgtgttggt cgagggttgg   4860
tccacagctt tgcaatcagg ccctccagcc acttcaatct ggtgtgagtt ggatgattcg   4920
gatttcggct caactgaaga tcaaaattcc ttgagcttcg aatatcttgg tgctttgaga   4980
ttcttgtcaa actccctggc gacaaccggt atcttatcgt gcatatctgt tggcccatca   5040
gcaccattcg aagattatgg tcacctctta gaccagccag gcctcataca gatggatgag   5100
gtgctagggt gcaagaactg ggccatgctg actatactcg aagtgggtaa gctggaccgg   5160
tggaagcgcc aggagcaaga gcacaaccgt ttgagcctaa agacactcgc taggcgtgca   5220
```

-continued

```
atgatgatag aggacatgtt gacagacgag ctacaaaagc ttccggcaag cgagacactg   5280

cctgatctca tcaaccatat ttacgccgcc tccattatga catacctgca tacagtagtt   5340

tcaggactca atcccaacct ttcagaggtc caggatagtg tgaacgcaac gattctattg   5400

ttggagagac tcccagatct gcaagctgtc gcgtctgtta cttggccttt ggctgtcaca   5460

ggttgcatgg cctcggaaag tcataaggac tttttcagaa atactctgag gtcctatgac   5520

gcgacattca cctcgttaaa aaagtatgat ggaactcttg aggttttgga agacgcttgg   5580

aacaaacgag agatagacag agagtctcca atcaggtggg aggatctgat ggatcaccat   5640

gggcttccag tgctcctact ctagggttgg tatcatcccc agacactcgt gctaccaaca   5700

cagagactgt ctttagtctt tattttgcat acgctacctg attcatgtaa gttcggtgtt   5760

cacttgccga cgatacatcc agggaagtct gactagtcag tgcttatggt tcgattcctt   5820

ttggcgttat aaaccggttc tgtcatgaag caagatatga tttcgatgag agggaagagc   5880

gaacaactat tcacatgtaa cttaaattat agactttcag tataaacttt cgattataag   5940

ccacacctaa tctaagtata tatatccaat caattgtacc aaaagtagtc tggaatcatg   6000

gttgtcaatc ggtgctgtgt tcctccatat tcttgacatg atttgacttg tccggtccgc   6060

gcgacacacg atgttgatca taatgaagga gtgttgattt tgagtaggaa aagatattgc   6120

agttccttgt aaagatcgtt cggaacgaaa cccggctgga gtatgatttg ttcgtggacc   6180

cgaagtgcaa aaatgccgga attaatgaca ggcattctct tcagttggct tgggttgaga   6240

tattggtctg cgtctgttgg aaagctgaca ttggatcttc aacatgcttt tgccgcgacc   6300

cagatggttg cgcataaggc agcgctgact cccgagtatg cgaaaacctc gagccacgaa   6360

acatcagggt ccatttccgt tgagtcgatc aatttagcgg ctgcgagcat cttgagagtt   6420

ttgggataag tctttgagtg gacaacagta atgtgatatg gtatgatctg atgtcgtgtt   6480

cgtgttgatg agaataaatt gttgagctga ttcccatcgg ctctgaccaa cagttaatat   6540

ctaaattctt ctactatcta tgcactatgg actggggagt caacgttgtt cgttctctgg   6600

agagaggcct aaatgatctt gaattggtgt gtaactgaaa cgtcagtaga aggcctgaat   6660

tcgcaagcgc cgaacttccg gcctacactg ccactgactt tgcggctcag catttagata   6720

gtgggcttca cagcgggtat tgtctcttct gcagcattgc tacggattta tcggcttcaa   6780

caacccttgc tgaaccaatg atgggttaca ttgatgggca ttcgttttta aacttttgtc   6840

aggttggcag aggcctaaaa tctgccgtcg gtgtgtgaga gaccatgaat caggcccctg   6900

cattaatgta gggcatttgc tagcccgcgg caagagcgca gaaagc                  6946
```

```
<210> SEQ ID NO 2
<211> LENGTH: 380
<212> TYPE: PRT
<213> ORGANISM: Fusarium

<400> SEQUENCE: 2

Met Glu Asn Phe Pro Thr Glu Tyr Phe Leu Asn Thr Ser Val Arg Leu
1               5                   10                  15

Leu Glu Tyr Ile Arg Tyr Arg Asp Ser Asn Tyr Thr Arg Glu Glu Arg
            20                  25                  30

Ile Glu Asn Leu His Tyr Ala Tyr Asn Lys Ala Ala His His Phe Ala
        35                  40                  45

Gln Pro Arg Gln Gln Gln Leu Leu Lys Val Asp Pro Lys Arg Leu Gln
    50                  55                  60

Ala Ser Leu Gln Thr Ile Val Gly Met Val Val Tyr Ser Trp Ala Lys
```

-continued

```
65                  70                  75                  80

Val Ser Lys Glu Cys Met Ala Asp Leu Ser Ile His Tyr Thr Tyr Thr
                85                  90                  95

Leu Val Leu Asp Asp Ser Ser Asp Asp Pro Tyr Pro Ala Met Met Asn
            100                 105                 110

Tyr Phe Asn Asp Leu Gln Ala Gly Arg Glu Gln Ala His Pro Trp Trp
        115                 120                 125

Ala Leu Val Asn Glu His Phe Pro Asn Val Leu Arg His Phe Gly Pro
    130                 135                 140

Phe Cys Ser Leu Asn Leu Ile Arg Ser Thr Leu Asp Phe Phe Glu Gly
145                 150                 155                 160

Cys Trp Ile Glu Gln Tyr Asn Phe Gly Gly Phe Pro Gly Ser His Asp
                165                 170                 175

Tyr Pro Gln Phe Leu Arg Arg Met Asn Gly Leu Gly His Cys Val Gly
            180                 185                 190

Ala Ser Leu Trp Pro Lys Glu Gln Phe Asp Glu Arg Gly Leu Phe Leu
        195                 200                 205

Glu Ile Thr Ser Ala Ile Ala Gln Met Glu Asn Trp Met Val Trp Val
    210                 215                 220

Asn Asp Leu Met Ser Phe Tyr Lys Glu Phe Asp Asp Glu Arg Asp Gln
225                 230                 235                 240

Ile Ser Leu Val Lys Asn Tyr Val Val Ser Asp Glu Ile Thr Leu His
                245                 250                 255

Glu Ala Leu Glu Lys Leu Thr Gln Asp Thr Leu His Ser Ser Lys Gln
            260                 265                 270

Met Val Ala Val Phe Ser Asp Lys Asp Pro Gln Val Met Asp Thr Ile
        275                 280                 285

Glu Cys Phe Met His Gly Tyr Val Thr Trp His Leu Cys Asp His Arg
    290                 295                 300

Tyr Arg Leu Asn Glu Ile Tyr Glu Lys Val Lys Gly Gln Lys Thr Glu
305                 310                 315                 320

Asp Ala Gln Lys Phe Cys Lys Phe Tyr Glu Gln Ala Ala Asn Val Gly
                325                 330                 335

Ala Val Ser Pro Ser Glu Trp Ala Tyr Pro Pro Ile Ala Gln Leu Ala
            340                 345                 350

Asn Ile Arg Ser Lys Asp Val Lys Asp Val Lys Asp Val Lys Glu Ile
        355                 360                 365

Gln Lys Pro Leu Leu Ser Ser Ile Glu Leu Val Glu
    370                 375                 380


<210> SEQ ID NO 3
<211> LENGTH: 20
<212> TYPE: DNA
<213> ORGANISM: Fusarium

<400> SEQUENCE: 3

ggctgctcat cactttgctc                                                20


<210> SEQ ID NO 4
<211> LENGTH: 20
<212> TYPE: DNA
<213> ORGANISM: Fusarium

<400> SEQUENCE: 4

tgcatgaagc actcaatcgt                                                20
```

-continued

```
<210> SEQ ID NO 5
<211> LENGTH: 377
<212> TYPE: PRT
<213> ORGANISM: Fusarium

<400> SEQUENCE: 5

Met Glu Asn Phe Pro Thr Glu Tyr Phe Leu Asn Thr Ser Val Arg Leu
 1               5                  10                  15

Leu Glu Tyr Ile Arg Tyr Arg Asp Ser Asn Tyr Thr Arg Glu Glu Arg
            20                  25                  30

Ile Glu Asn Leu His Tyr Ala Tyr Asn Lys Ala Ala His His Phe Ala
        35                  40                  45

Gln Pro Arg Gln Gln Gln Leu Leu Lys Val Asp Pro Lys Arg Leu Gln
    50                  55                  60

Ala Ser Leu Gln Thr Ile Val Gly Met Val Val Tyr Ser Trp Ala Lys
65                  70                  75                  80

Val Ser Lys Glu Cys Met Ala Asp Leu Ser Ile His Tyr Thr Tyr Thr
                85                  90                  95

Leu Val Leu Asp Asp Ser Ser Asp Asp Pro Tyr Ala Ala Met Met Asn
            100                 105                 110

Tyr Phe Asn Asp Leu Gln Ala Gly Arg Glu Gln Ala His Pro Trp Trp
        115                 120                 125

Ala Leu Val Asn Glu His Phe Pro Asn Val Leu Arg His Phe Gly Pro
    130                 135                 140

Phe Cys Ser Leu Asn Leu Ile Arg Ser Thr Leu Asp Phe Phe Glu Gly
145                 150                 155                 160

Cys Trp Ile Glu Gln Tyr Asn Phe Gly Gly Phe Pro Gly Ser His Asp
                165                 170                 175

Tyr Pro Gln Phe Leu Arg Arg Met Asn Gly Leu Gly His Cys Val Gly
            180                 185                 190

Ala Ser Leu Trp Pro Lys Glu Gln Phe Asp Glu Arg Ser Leu Phe Leu
        195                 200                 205

Glu Ile Thr Ser Ala Ile Ala Gln Met Glu Asn Trp Met Val Trp Val
    210                 215                 220

Asn Asp Leu Met Ser Phe Tyr Lys Glu Phe Asp Asp Glu Arg Asp Gln
225                 230                 235                 240

Ile Ser Leu Val Lys Asn Tyr Val Val Ser Asp Glu Ile Ser Leu His
                245                 250                 255

Glu Ala Leu Glu Lys Leu Thr Gln Asp Thr Leu His Ser Ser Lys Gln
            260                 265                 270

Met Val Ala Val Phe Ser Asp Lys Asp Pro Gln Val Met Val Thr Ile
        275                 280                 285

Glu Cys Phe Met His Gly Tyr Val Thr Trp His Leu Cys Asp His Arg
    290                 295                 300

Tyr Arg Leu Asn Glu Ile Ser Glu Lys Val Lys Glu Gln Lys Thr Glu
305                 310                 315                 320

Asp Ala Gln Lys Phe Cys Lys Phe Tyr Glu Gln Ala Ala Asn Val Gly
                325                 330                 335

Ala Val Ser Pro Ser Glu Trp Ala Tyr Pro Pro Val Ala Gln Leu Ala
            340                 345                 350

Asn Val Arg Ser Lys Asp Val Lys Asn Val Lys Gln Ile Glu Lys Pro
        355                 360                 365

Leu Leu Ser Ser Ile Glu Leu Val Glu
    370                 375
```

<210> SEQ ID NO 6
<211> LENGTH: 30
<212> TYPE: DNA
<213> ORGANISM: Fusarium

<400> SEQUENCE: 6
gagctcgagg aattcttaca aaccttcaac 30

<210> SEQ ID NO 7
<211> LENGTH: 47
<212> TYPE: DNA
<213> ORGANISM: Fusarium

<400> SEQUENCE: 7
ttaattaagg tacctgaatt taaatggtga agagatagat atccaag 47

<210> SEQ ID NO 8
<211> LENGTH: 51
<212> TYPE: DNA
<213> ORGANISM: Fusarium

<400> SEQUENCE: 8
tcaccattta aattcaggta ccttaattaa attccttgtt ggaagcgtcg a 51

<210> SEQ ID NO 9
<211> LENGTH: 42
<212> TYPE: DNA
<213> ORGANISM: Fusarium

<400> SEQUENCE: 9
tggtatgcat aagcttgaat tcaggtaaac aagatataat tt 42

<210> SEQ ID NO 10
<211> LENGTH: 26
<212> TYPE: DNA
<213> ORGANISM: Fusarium

<400> SEQUENCE: 10
ccaccatggt cggctttacc cccgtt 26

<210> SEQ ID NO 11
<211> LENGTH: 31
<212> TYPE: DNA
<213> ORGANISM: Fusarium

<400> SEQUENCE: 11
ggttaattaa ttagcccacg tcagcaacgg t 31

<210> SEQ ID NO 12
<211> LENGTH: 20
<212> TYPE: DNA
<213> ORGANISM: Fusarium

<400> SEQUENCE: 12
aactggaaag acctgtgggc 20

<210> SEQ ID NO 13
<211> LENGTH: 21
<212> TYPE: DNA
<213> ORGANISM: Fusarium

<400> SEQUENCE: 13

-continued gggaaatagt gtcacgcggt a 21

<210> SEQ ID NO 14
<211> LENGTH: 21
<212> TYPE: DNA
<213> ORGANISM: Fusarium

<400> SEQUENCE: 14
ggacaacagc cgaactcaaa c 21

<210> SEQ ID NO 15
<211> LENGTH: 18
<212> TYPE: DNA
<213> ORGANISM: Fusarium

<400> SEQUENCE: 15
gtgctgcgga taaggttc 18

<210> SEQ ID NO 16
<211> LENGTH: 20
<212> TYPE: DNA
<213> ORGANISM: Fusarium

<400> SEQUENCE: 16
cggtatcgaa tgtactcgag 20

<210> SEQ ID NO 17
<211> LENGTH: 17
<212> TYPE: DNA
<213> ORGANISM: Fusarium

<400> SEQUENCE: 17
cccatggtgt gaacacc 17

<210> SEQ ID NO 18
<211> LENGTH: 13
<212> TYPE: DNA
<213> ORGANISM: Fusarium

<400> SEQUENCE: 18
gatcgattta aat 13

<210> SEQ ID NO 19
<211> LENGTH: 13
<212> TYPE: DNA
<213> ORGANISM: Fusarium

<400> SEQUENCE: 19
tcgaatttaa atc 13

<210> SEQ ID NO 20
<211> LENGTH: 40
<212> TYPE: DNA
<213> ORGANISM: Fusarium

<400> SEQUENCE: 20
cgaatttcat atttaaatgc cgaccagcag acggccctcg 40

<210> SEQ ID NO 21
<211> LENGTH: 30
<212> TYPE: DNA
<213> ORGANISM: Fusarium

<400> SEQUENCE: 21

-continued gcgatatcat gatctctctg gtactcttcg 30

<210> SEQ ID NO 22
<211> LENGTH: 30
<212> TYPE: DNA
<213> ORGANISM: Fusarium

<400> SEQUENCE: 22
gcgatatcat cgaccagcag acggccctcg 30

<210> SEQ ID NO 23
<211> LENGTH: 32
<212> TYPE: DNA
<213> ORGANISM: Fusarium

<400> SEQUENCE: 23
gcgtttaaac atgatctctc tggtactctt cg 32

<210> SEQ ID NO 24
<211> LENGTH: 18
<212> TYPE: DNA
<213> ORGANISM: Fusarium

<400> SEQUENCE: 24
ggtagcacga gtgtctgg 18